United States Patent [19]
Hornback et al.

[11] Patent Number: 6,156,924
[45] Date of Patent: *Dec. 5, 2000

[54] ANTI-VIRAL COMPOUNDS

[75] Inventors: William J. Hornback, Fishers; Scott C. Mauldin; John E. Munroe, both of Indianapolis, all of Ind.

[73] Assignee: Eli Lilly and Company, Indianapolis, Ind.

[*] Notice: This patent is subject to a terminal disclaimer.

[21] Appl. No.: 09/214,530

[22] PCT Filed: May 2, 1997

[86] PCT No.: PCT/US97/07438

§ 371 Date: Jan. 6, 1999

§ 102(e) Date: Jan. 6, 1999

[87] PCT Pub. No.: WO97/42156

PCT Pub. Date: Nov. 13, 1997

Related U.S. Application Data

[60] Provisional application No. 60/016,901, May 6, 1996.

[51] Int. Cl.[7] .................. C07C 249/02; C07C 249/04

[52] U.S. Cl. ............... 560/43; 560/35; 562/440; 564/248; 564/251

[58] Field of Search ............ 560/35, 43; 562/440; 564/248, 251

[56] References Cited

U.S. PATENT DOCUMENTS

| | | |
|---|---|---|
| 2,703,809 | 3/1955 | Ritchie . |
| 2,744,100 | 5/1956 | Subluskey . |
| 2,744,102 | 5/1956 | Subluskey . |
| 2,750,382 | 12/1956 | Bible et al. . |
| 2,750,405 | 6/1956 | Ritchie et al. . |
| 2,750,407 | 6/1956 | Ritchie . |
| 2,753,357 | 7/1956 | Bible et al. . |
| 2,759,014 | 8/1956 | Bible . |
| 2,767,162 | 10/1956 | Picha . |
| 2,854,474 | 9/1958 | Bible . |
| 2,862,955 | 12/1958 | Hoehn . |
| 2,947,778 | 8/1960 | Bible . |
| 3,014,957 | 12/1961 | Hoehn . |
| 3,038,930 | 6/1962 | Bible . |
| 3,668,223 | 6/1972 | Jones . |
| 4,252,804 | 2/1981 | Joullie et al. . |
| 4,333,941 | 6/1982 | Baratz et al. . |
| 5,015,644 | 5/1991 | Roth et al. . |
| 5,276,053 | 1/1994 | Johnson . |
| 5,321,044 | 6/1994 | Peters et al. . |

FOREIGN PATENT DOCUMENTS

| | | |
|---|---|---|
| 0 540 143 A2 | 8/1992 | European Pat. Off. . |
| 0 806 203 A2 | 5/1997 | European Pat. Off. . |
| WO 97 41822 | 11/1997 | European Pat. Off. . |
| WO 97 41860 | 11/1997 | European Pat. Off. . |
| WO 97 41861 | 11/1997 | European Pat. Off. . |
| WO 97 42145 | 11/1997 | European Pat. Off. . |
| WO 97 42155 | 11/1997 | European Pat. Off. . |
| WO 97 42156 | 11/1997 | European Pat. Off. . |

OTHER PUBLICATIONS

UEDA, et al.: "The Leaf Oil and Resin Acid Components of Lacebark Pine, *Pinus bungeana* Zucc." Tottori Daigaku Kogakubu Kenkyu Hokiku, vol. 20, No. 1, 1989 Japan, pp. 87–96.

Caplus Abstr., No. 74:112247, Turner, et al., J. Chem. Soc. C., 1971, vol. 3, 547–553.

Caplus Abstr., No. 81:169653, Cambie, et al., Aust. J. Chem., 1974, vol. 27, No. 9, 2001–2016.

Caplus Abstr., No. 85:177668, Tahara, et al., Chem. Pharm. Bull., 1976, vol. 24, No. 7, 1497–1501.

Caplus Abstr., No. 121:116357, Standley, et al., J. Atmos. Chem., 1994, vol. 18, No. 1, 1–15.

Caplus Abstr., No. 124:317517, Matsumoto, et al., Chem. Pharm. Bull., 1996, vol. 44, No. 3, 530–533.

Caplus Abstr., No. 99:212742, Burnell, et al., Can. J. Chem., 1983, vol. 61, No. 11, 2461–2465.

Caplus Abstr., No. 102:79171, Burnell, et al., Synth. Commun., 1984, vol. 14, No. 13, 1229–1237.

Caplus Abstr., No. 113:152784, Cambie, et al., Aust. J. Chem., 1990, vol. 43, No. 5, 883–893.

Caplus Abstr., No. 121:35902, Matsumoto, et al., Chem. Pharm. Bull., 1993, vol. 41, No. 11, 1960–1964.

Chemical Abstracts, Abstract #2502; vol. 50, No. 4, Feb. 25, 1956, Michitoshi Ohta.

G. Defaye–Duchateau, "Oxydations dans la serie de l'acide dehydroabietique," 1964, Paris, 1469–1473.

Georges Dupont, et al., "Oxydation de l'acide abietique par l'acetate mercurique.Derives de l'acide dehydroabietique substitutes dans le cycle B," 1955, Paris, 708–715.

J. C. Sircar, et al., "Free–Radical Bromination of Methyl Abietate by N–Bromosuccinimide and Solvolysis of the Products,", vol. 35, No. 9, Sep., 1970, 3090–3093.

Chem. Abstr., vol. 112, No. 12, May 21, 1990, Abstract No. 198830, Sugai, et al.

Chem. Abstr., vol. 110, No. 9, Feb. 27, 1989, Abstract No. 75825, Nishi, et al.

Chem. Abstr., vol. 91, No. 23, Dec. 3, 1979, Abstract No. 193454, Pelletier, et al.

Chem. Abstr., vol. 81, No. 7, Aug. 19, 1994, Abstract No. 25842, Wirthlin, et al.

Chem. Abstr., vol. 121, No. 17, Oct. 24, 1974, Abstract No. 195010, Tagat, et al.

Chem. Abstr., vol. 120, No. 11, Mar. 14, 1994, Abstract No. 134850, Selwood, et al.

Chem. Abstr., vol. 61, No. 5, Aug. 31, 1964, Abstract No. 5699f, Tahara, et al.

Helvetica Chemica Acta., vol. 57, No. 2, Mar. 13, 1974, Basel Ch., 351–368.

Tetrahedron, vol. 21, No. 8, Aug. 1965, Oxford GB, 2133–2154.

(List continued on next page.)

*Primary Examiner*—Jane Fan
*Attorney, Agent, or Firm*—Arlene K. Musser

[57] ABSTRACT

The present invention provides compounds which inhibit an envelope virus by inhibiting the fusion of the virus with the host cell. The virus may be inhibited in an infected cell, a cell susceptible of infection or a mammal in need thereof.

7 Claims, No Drawings

OTHER PUBLICATIONS

Database Crossfire, Beilstein Informationssysteme, GMBH. Frankfurt DE, Beilstein registry No. 5483432, XP002061126, Cruz Frederico G., et al., Phytochemistry, vol. 31, No. 8, 1992, pp. 2793–2796.

Chem. Abstr., vol. 110, No. 21, Nov. 20, 1989, Abstract No., 195166, Node, et al.

Chem. Abstr., vol. 88, No. 25, Jun. 19, 1978, Abstract No. 191065, Ichinohe.

Chem. Abstr., vol. 83, No. 11, Sep. 15, 1975, Abstract No. 97643, Ichinohe.

Chem. Abstr., vol. 81, No. 5, Aug. 5, 1974, Abstract No. 25842, Wirthlin, et al.

Database Crossfire, Beilstein Informationssysteme, GMBH. Frankfort DE, Beilstein registry No. 4824891, XP002060909, Richard C. Cambie, et al., Australian Journal of Chemistry, vol. 44, No. 11, 1991, pp. 1553–1573.

Database Crossfire, Beilstein Informationssysteme, GMBH. FrankfUrt DE, Beilstein registry No. 2179057, XP002060813, Richard C. Cambie, et al., Australian Journal of Chemistry, vol. 27, 1974, pp. 2413–2419.

Database Crossfire, Beilstein Informationssysteme, GMBH. FrankfUrt DE, Beilstein registry No. 2887142, XP002060814, Richard C. Cambie, et al., Australian Journal of Chemistry, vol. 25, 1972, pp. 974–980.

Database Crossfire, Beilstein Informationsysteme, GMBH. FrankfUrt DE, Beilstein registry No. 2920097, XP002060815, Richard C. Cambie, et al., Australian Journal of Chemistry, vol. 27, 1974, pp. 2001–2011.

Comptes Rendus De l'academie Bulgare des Sciences, vol. 48, No. 11–12, 1995.

ANTI-VIRAL COMPOUNDS

CROSS-REFERENCE

This application is a 371 of PCT/US97/07438 filed on May 2, 1997 which claims the benefit of U.S. Provisional Patent Application Ser. No. 60/016,901 filed on May 6, 1996.

Influenza viruses cause an infectious disease for which there is no adequate therapeutic agent. The disadvantages of existing treatments include the onset of clinical resistance within thirty six hours and the ineffectiveness of the agents against influenza B. Killed influenza virus vaccines have been available for over sixty years. However, these vaccines have not lessened the morbidity, mortality or severe financial loss caused by this disease. It follows that an agent which treats or prevents an influenza infection or is effective at preventing the clinical symptoms associated with an influenza infection will result in a significant benefit to society.

Currently, the only compounds approved for the therapeutic and prophylactic treatment of influenza infections are the adamantanes: amantadine and rimantadine. These compounds inhibit influenza A by inhibiting the function of the M2 ion channel activity of the virus. Amantadine is a potent in vitro inhibitor of influenza A virus as demonstrated by standard antiviral assays such as the plaque reduction assay. Amantadine is effective in reducing the duration of fever and other systemic complaints including but not limited to myalgia (muscular ache) and fatigue when administered to individuals infected with influenza A within forty-eight hours of the onset of clinical symptoms. It has also been observed that amantadine results in a one hundred-fold decrease of virus titer in the nasal washes of human volunteers infected with wild-type influenza virus which correlates with a dramatic decrease in fever score. Thus, in vitro influenza inhibition is predictive of useful in vivo effects, i.e. a reduction of the clinical symptoms associated with the influenza infection.

The present invention derives from the fact that influenza is an enveloped virus which dictates that the virus envelope must be fused with the endosomal membrane of the host cell in order to initiate the process of introducing its genetic information into the cell. Because this process is common to all enveloped viruses, it is an attractive target for antiviral chemotherapy. Examples of envelope viruses which are inhibited according to the present invention include influenza, bovine diarrheal, hepatitis C, tick borne encephalitis and the like. The fusion domain of the envelope glycoprotein of influenza, hemagglutinin (HA) has been well-characterized. See, White J. M., Annu. Rev. Physiol. vol. 52, pages 675–697 (1990) which is herein incorporated by reference.

Influenza virus HA provides at least two distinct functions: 1) recognition of the host cell receptor, i.e., sialic acid residues on glycoconjugates, and 2) fusion of the viral envelope with the endosomal membrane. Both functions are essential for the propagation of influenza virus in vitro and in vivo. During viral maturation, monomeric HA is inserted into a lipid bilayer, post-translationally modified and oligomerized into a trimer of identical subunits (trimeric HA). The infectivity of the progeny virus is contingent upon a site-specific cleavage of HA by host cell protease(s). This cleavage results in the formation of two polypeptide chains, HA1 and HA2, which remain associated by non-covalent interactions as well as by an intermolecular and intramolecular disulfide bonds.

It has been established that influenza HA has two functionally relevant conformations. One conformation (Form A) exists as a metastable structure at neutral pH and mediates receptor recognition. Following receptor mediated binding to the host cell, the virus is transported to the endosomal compartment where it encounters an acidic environment. The low pH triggers a dramatic structural rearrangement of HA (Form A) which results in the formation of the other, more stable conformation of HA (Form B).

Form B of HA is required for fusion of the virus envelope with the endosomal membrane. It is the structural rearrangement from Form A to Form B of HA that allows the fusion domain of HA to directly interact with the endosomal membrane enabling the release of viral genetic information into the host cell cytoplasm. These considerations lend themselves to the development of a strategy for antiviral intervention based on the abrogation of HA-mediated fusion of virus-host membranes.

The present invention relates to a compound of the formula:

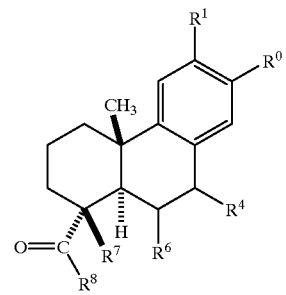

I wherein:

$R^0$ and $R^1$ are independently hydrogen, hydroxy, $C_1$–$C_6$ alkyl, $C_1$–$C_6$ alkoxy, hydroxy($C_1$–$C_6$ alkyl), sulfhydryl, sulfamyl, —$SO_2$—Cl, —S—C(O)—N(CH$_3$)$_2$, amino, $C_1$–$C_4$ alkylamino, di($C_1$–$C_4$ alkyl)amino, $C_1$–$C_4$ alkylsulfonylamino, di($C_1$–$C_4$ alkylsulfonyl)amino —$X^0$—O—C(O)—$C_1$–$C_4$ alkyl, —O—$(X^1)_i$—$X^2$, —C(O)—$X^3$, —N—C(O)—$R^2$ or —O—$R^3$;

$X^0$ is a bond or divalent($C_1$–$C_6$ alkyl);

$X^1$ is an amino acid;

$X^2$ is hydrogen or an amino protecting group;

i is 1, 2 or 3;

$X^3$ is $C_1$–$C_6$ alkyl, $C_1$–$C_6$ alkoxy, halo($C_1$–$C_6$ alkyl), hydroxy($C_1$–$C_6$ alkyl) or phenyl;

$R^2$ is $C_1$–$C_4$ alkyl, $C_1$–$C_4$ alkoxy, halo($C_1$–$C_4$ alkyl), hydroxy($C_1$–$C_4$ alkyl), phenyl, p-methoxy-phenyl, p-fluoro-phenyl, naphthyl, pyridyl, piperidinyl, thiazolyl, oxazolyl, thienyl, furyl, tetrahydrofuryl or cyclohexyl;

$R^3$ is $C_1$–$C_6$ alkenyl, —$CH_2$—$R^{3a}$, —C(O)—$R^{3b}$, —C(S)—$R^{3c}$, —C(CH$_3$)$_2$C(O)NH$_2$, phenyl or a group of the formula:

$R^{3a}$ is phenyl, p-fluorophenyl, pyridyl, pyrrolidinyl, piperidinyl, piperazinyl, morpholinyl, N-($C_1$–$C_4$ alkoxycarbonyl)piperidinyl, N-(trifluoromethyl)-piperidinyl, thiazolyl, oxazolyl, imidazolyl, isothiazolyl, isooxazolyl, quinolyl, isoquinolyl, thienyl, furyl, tetrahydrothienyl, tetrahydrofuryl, cyclohexyl, cyclopentyl, cyclopropyl or naphthyl;

$R^{3b}$ is pyrrolidinyl, piperidinyl, piperazinyl, morpholinyl, N-($C_1$–$C_4$ alkoxycarbonyl)piperidinyl, N-(trifluoromethyl)piperidinyl, benzyloxy, pyridylmethyloxy, $C_1$–$C_6$ alkoxy, halo($C_1$–$C_4$ alkoxy), amino, $C_1$–$C_4$ alkylamino or di($C_1$–$C_4$ alkyl)amino;

$R^{3c}$ is amino, $C_1$–$C_4$ alkylamino or di($C_1$–$C_4$ alkyl)amino;

$R^{3d}$ is oxygen, hydroximino, hydrazino or =CHZ;

Z is hydrogen, $C_1$–$C_4$ alkyl, halogen, di($C_1$–$C_4$ alkyl)amino, $C_1$–$C_4$ alkoxycarbonyl, carbamoyl($C_1$–$C_4$ alkyl), N-($C_1$–$C_4$ alkyl)carbamoyl or N,N-di($C_1$–$C_4$ alkyl)carbamoyl;

$R^{3e}$ is hydrogen, nitro or trifluoromethyl;

X is a bond or —($CH_2$)—;

$R^4$ is hydrogen, hydroxy, amino, $C_1$–$C_4$ alkylamino, di($C_1$–$C_4$ alkyl)amino, $C_1$–$C_4$ alkoxy, =O, —O—S($CH_3$)$_2$C ($CH_3$)$_3$, $C_2$–$C_6$ alkanoyloxy, N-($C_2$–$C_6$ alkanoyl)amino, =N—$R^5$ or $R^4$ and $R^6$ combine to form a bond;

$R^5$ is hydroxy, amino, $C_1$–$C_4$ alkylamino, di($C_1$–$C_4$ alkyl)amino, $C_1$–$C_4$ alkoxy, pyridylmethoxy, benzyloxy, piperazinyl, N-(methyl)piperazinyl or —O—$CH_2$—C(O)—$R^{5a}$;

$R^{5a}$ is hydroxy or $C_1$–$C_4$ alkoxy;

$R^6$ is hydrogen, halo, $C_1$–$C_4$ alkyl or =O;

$R^7$ is hydrogen or $C_1$–$C_4$ alkyl;

$R^8$ is hydroxy, halo, $C_1$–$C_6$ alkoxy, pyrrolidinyl, piperidinyl, piperazinyl, 4-methyl-piperazinyl, morpholinyl or —N($R^9$)—$R^{10}$;

$R^9$ is hydrogen or methyl;

$R^{10}$ is —(divalent $C_1$–$C_6$ alkyl)—$R^{10a}$;

$R^{10a}$ is pyridyl, with the proviso that i) when $R^4$ is hydrogen or =O; $R^8$ is methoxy; and $R^1$ is hydrogen; then $R^0$ cannot be hydrogen, hydroxy, isopropyl, methoxy, —C($CH_3$)$_2$OH, —C(O)$CH_3$ or —OC(O)$CH_3$;

ii) when $R^4$ is hydrogen or =O; $R^8$ is methoxy; and $R^0$ is isopropyl; then $R^1$ cannot be hydroxy or methoxy;

iii) when $R^4$ is hydrogen or =O; $R^8$ is hydroxy; and $R^0$ is hydrogen; then $R^1$ cannot be hydrogen or isopropyl;

iv) when $R^4$ is hydrogen; $R^8$ is methoxy; and $R^0$ is hydrogen; then $R^1$ cannot be hydrogen, hydroxy, —C(O)$CH_3$ or —OC(O)$CH_3$;

or a pharmaceutically acceptable salt thereof.

The present invention provides new compounds of formula I, as described above, that are useful for treating or preventing a viral infection where the virus is an envelope virus that undergoes hemagglutinin-mediated fusion with a host cell and/or the resultant symptoms. These compounds, their pharmaceutically acceptable salts and the corresponding pharmaceutical formulations can be used alone or in combination with other antivirals, immunomodulators, antibiotics or vaccines.

All temperatures stated herein are in degrees Celsius (° C.). All units of measurement employed herein are in weight units except for liquids which are in volume units.

The term "halo" represents chloro, fluoro, bromo or iodo.

The term "$C_1$–$C_6$ alkyl" represents a straight or branched alkyl chain having from one to six carbon atoms. Typical $C_1$–$C_6$ alkyl groups include methyl, ethyl, propyl, isopropyl, butyl, isobutyl, sec-butyl, t-butyl and the like. The term "$C_1$–$C_6$ alkyl" includes within its definition the term "$C_1$–$C_4$ alkyl."

The term "halo($C_1$–$C_6$)alkyl" represents a straight or branched alkyl chain having from one to six carbon atoms with 1, 2 or 3 halogen atoms attached to it. Typical halo ($C_1$–$C_6$)alkyl groups include chloromethyl, 2-bromoethyl, 1-chloroisopropyl, 3-fluoropropyl, 2,3-dibromobutyl, 3-chloroisobutyl, iodo-t-butyl, trifluoromethyl and the like.

The term "hydroxy($C_1$–$C_6$)alkyl" represents a straight or branched alkyl chain having from one to six carbon atoms with an hydroxy group attached to it. Typical hydroxy ($C_1$–$C_6$)alkyl groups include hydroxymethyl, 2-hydroxyethyl, 1-hydroxyisopropyl, 2-hydroxypropyl, 2-hydroxybutyl, 3-hydroxyisobutyl, hydroxy-t-butyl, hydroxypentyl and the like.

The term "$C_1$–$C_4$ alkylamino" represents a straight or branched alkylamino chain having from one to four carbon atoms attached to an amino group. Typical $C_1$–$C_4$ alkylamino groups include methylamino, ethylamino, propylamino, isopropylamino, butylamino, sec-butylamino and the like.

The term "di($C_1$–$C_4$)alkylamino" represents a straight or branched dialkylamino chain having two alkyl chains, each having independently from one to four carbon atoms attached to a common amino group. Typical di($C_1$–$C_4$) alkylamino groups include dimethylamino, ethylmethylamino, methylisopropyl-amino, t-butylisopropylamino, di-t-butylamino and the like.

The term "$C_1$–$C_6$ alkoxy" represents a straight or branched alkyl chain having from one to six carbon atoms attached to an oxygen atom. Typical $C_1$–$C_6$ alkoxy groups include methoxy, ethoxy, propoxy, isopropoxy, butoxy, t-butoxy, pentoxy and the like. The term "$C_1$–$C_6$ alkoxy" includes within its definition the term "$C_1$–$C_4$ alkoxy".

The term "$C_2$–$C_6$ alkenyl" represents a straight or branched alkenyl chain having from two to six carbon atoms. Typical $C_2$–$C_6$ alkenyl groups include ethenyl, propenyl, isopropenyl, buten-2-yl, t-butenyl, penten-1-yl, hexen-3-yl, 3-methylpentenyl and the like.

The term "$C_1$–$C_4$ alkoxycarbonyl" represents a straight or branched alkoxy chain having from one to four carbon atoms attached to a carbonyl moiety. Typical $C_1$–$C_4$ alkoxycarbonyl groups include methoxycarbonyl, ethoxycarbonyl, propoxycarbonyl, isopropoxycarbonyl, butoxycarbonyl, t-butoxycarbonyl and the like.

The term "carbamoyl($C_1$–$C_4$)alkyl" represents a straight or branched alkyl chain having from one to four carbon atoms with a carbamoyl group attached to it. Typical carbamoyl($C_1$–$C_4$)alkyl groups include carbamoylmethyl, carbamoylethyl, carbamoylpropyl, carbamoylisopropyl, carbamoylbutyl and carbamoyl-t-butyl and the like.

The term "N-($C_1$–$C_4$)alkylcarbamoyl" represents a straight or branched alkyl chain having from one to four carbon atoms attached to the nitrogen atom of a carbamoyl moiety. Typical N-(C$_1$–C$_4$ alkyl)carbamoyl groups include N-methylcarbamoyl, N-ethylcarbamoyl, N-propylcarbamoyl, N-isopropylcarbamoyl, N-butylcarbamoyl, N-t-butylcarbamoyl and the like.

The term "N,N-di(C$_1$–C$_4$ alkyl)carbamoyl" represents a straight or branched alkyl chain having a straight or branched C$_1$–C$_4$ alkyl chain attached to each of the nitrogen atoms on a carbamoyl moiety. Typical N-(C$_1$–C$_4$) alkylcarbamoyl groups include N,N-dimethylcarbamoyl, N-ethyl-N-methylcarbamoyl, N-propyl-N-butylcarbamoyl, N,N-diisopropylcarbamoyl, N-methyl-N-butylcarbamoyl and the like.

The term "C$_1$–C$_4$ alkylsulfonylamino" represents a straight or branched alkyl group having from one to four carbon atoms attached to a sulfonylamino moiety. Typical C$_1$–C$_4$ alkylsulfonylamino groups include methylsulfonylamino, ethylsulfonylamino, propylsulfonylamino, isopropylsulfonyl-amino, butylsulfonylamino, isobutylsulfonylamino, sec-butylsulfonylamino and t-butylsulfonylamino.

The term "di(C$_1$–C$_4$ alkylsulfonyl)amino" represents two C$_1$–C$_4$ alkylsulfonyl moieties attached to an amino moiety. Typical di(C$_1$–C$_4$ alkylsulfonyl)amino groups include methylmethylsulfonylamino, ethylmethylsulfonylamino, propylethylsulfonylamino, isopropylmethylsulfonylamino, t-butylethylsulfonylamino, butylbutylsulfonylamino and the like.

The term "C$_2$–C$_6$ alkanoyl" represents a straight or branched alkyl chain having from one to five carbon atoms attached to a carbonyl moiety. Typical C$_2$–C$_6$ alkanoyl groups include ethanoyl, propanoyl, isopropanoyl, butanoyl, t-butanoyl, pentanoyl, hexanoyl, 3-methylpentanoyl and the like.

The term "C$_2$–C$_6$ alkanoyloxy" represents a straight or branched alkyl group having from one to five carbon atoms attached to a carbonyloxy moiety. Typical C$_2$–C$_6$ alkanoyloxy groups include ethanoyloxy, propanoyloxy, isopropanoyloxy, butanoyloxy, isobutanoyloxy, sec-butanoyloxy, t-butanoyloxy, pentanoyloxy and the like.

The term "C$_2$–C$_6$ alkanoylamino" represents a straight or branched alkyl group one to five carbon atoms attached to a carbonylamino moiety. Typical C$_2$–C$_6$ alkanoylamino groups include ethanoylamino, propanoylamino, isopropanoylamino, butanoyl-amino, isobutanoylamino, sec-butanoylamino, t-butanoylamino, pentanoylamino and the like.

As mentioned above, the invention includes the pharmaceutically acceptable salts of the compounds defined by formula I. Although generally neutral, a compound of this invention can possess a sufficiently acidic, a sufficiently basic, or both functional groups, and accordingly react with any of a number of inorganic bases, and inorganic and organic acids, to form a pharmaceutically acceptable salt.

The term "pharmaceutically acceptable salt" as used herein, refers to salts of the compounds of the above formula which are substantially non-toxic to living organisms. Typical pharmaceutically acceptable salts include those salts prepared by reaction of the compounds of the present invention with a mineral or organic acid or an inorganic base. Such salts are known as acid addition and base addition salts.

Acids commonly employed to form acid addition salts are inorganic acids such as hydrochloric acid, hydrobromic acid, hydroiodic acid, sulfuric acid, phosphoric acid and the like, and organic acids such as p-toluenesulfonic, methanesulfonic acid, oxalic acid, p-bromophenylsulfonic acid, carbonic acid, succinic acid, citric acid, benzoic acid, acetic acid, and the like.

Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, δ-hydroxybutyrate, glycollate, tartrate, methanesulfonate, propanesulfonate, naphthalene-1-sulfonate, napththalene-2-sulfonate, mandelate and the like. Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole.

The term "amino-protecting group" as used in the specification refers to substituents of the amino group commonly employed to block or protect the amino functionality while reacting other functional groups on the compound. Examples of such amino-protecting groups include formyl, trityl, phthalimido, trichloroacetyl, chloroacetyl, bromoacetyl, iodoacetyl groups, or urethane-type blocking groups such as benzyloxycarbonyl, 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxycarbonyl, t-butoxycarbonyl, 2-(4-xenyl) isopropoxycarbonyl, 1,1-diphenyleth-1-yloxycarbonyl, 1,1-diphenylprop-1-yloxycarbonyl, 2-phenylprop-2-yloxycarbonyl, 2-(p-toluyl)-prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluylsulfonyl)-ethoxycarbonyl, 2-(methylsulfonyl)ethoxycarbonyl, 2-(triphenylphosphino)-ethoxycarbonyl, fluorenylmethoxy-carbonyl ("FMOC"), 2-(trimethylsilyl)ethoxycarbonyl, allyloxycarbonyl, 1-(trimethylsilylmethyl)prop-1-enyloxycarbonyl, 5-benzisoxalylmethoxycarbonyl, 4-acetoxybenzyloxycarbonyl, 2,2,2-trichloroethoxycarbonyl, 2 -ethynyl-2-propoxycarbonyl, cyclopropylmethoxycarbonyl, 4-(decyloxy) benzyloxycarbonyl, isobornyloxycarbonyl, 1-piperidyloxycarbonyl and the like; benzoylmethylsulfonyl, 2-nitrophenylsulfenyl, diphenylphosphine oxide and like amino-protecting groups. The species of amino-protecting group employed is not critical so long as the derivatized amino group is stable to the condition of subsequent reaction(s) on other positions of the intermediate molecule and can be selectively removed at the appropriate point without disrupting the remainder of the molecule including any other amino-protecting group(s). Preferred amino-protecting groups are t-butoxycarbonyl (t-Boc), allyloxycarbonyl and benzyloxycarbonyl (CbZ). Further examples of groups referred to by the above terms are described by J. W. Barton, "Protective Groups in Organic Chemistry", J. G. W. McOmie, Ed., Plenum Press, New York, N.Y., 1973, Chapter 2, and T. W. Greene, "Protective Groups in Organic Synthesis", John Wiley and sons, New York, N.Y., 1981, Chapter 7.

The term "carboxy-protecting group" as used in the specification refers to substituents of the carboxy group commonly employed to block or protect the carboxy functionality while reacting other functional groups on the compound. Examples of such carboxy-protecting groups include methyl, p-nitrobenzyl, p-methylbenzyl, p-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxy-benzhydryl, 2,2',4,4'-tetramethoxybenzhydryl, t-butyl, t-amyl, trityl, 4-methoxytrityl, 4,4'-dimethoxytrityl, 4,4',4"-trimethoxytrityl, 2-phenylprop-2-yl, trimethylsilyl, t-butyldimethylsilyl, phenacyl, 2,2,2-trichloroethyl, β(dibutylmethylsilyl)ethyl, p-toluenesulfonylethyl, 4-nitrobenzylsulfonylethyl, allyl, cinnamyl, 1-(trimethylsilylmethyl)prop-1-en-3-yl and like moieties. Preferred carboxy-protecting groups are allyl, benzyl and t-butyl. Further examples of these groups are found in E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, N.Y., 1981, Chapter 5.

Preferred compounds are those compounds of formula I where:

$R^0$ is hydrogen, hydroxy, $C_1$–$C_6$ alkyl, $C_1$–$C_6$ alkoxy, hydroxy($C_1$–$C_6$ alkyl), —$X^0$—O—C(O)—$C_1$–$C_4$ alkyl, —O—$(X^1)_i$—$X^2$, —C(O)—$X^3$ or —O—$R^3$;

$R^1$ is hydrogen, hydroxy, $C_1$–$C_6$ alkoxy, sulfhydryl, sulfamyl, —$SO_2$—Cl, amino, di($C_1$–$C_4$ alkylsulfonyl)amino, —C(O)—$X^3$, —N—C(O)—$R^2$ or —O—$R^3$;

$X^0$ is a bond or divalent($C_1$–$C_6$ alkyl);

$X^1$ is an amino acid;

$X^2$ is hydrogen or an amino protecting group;

i is 1 or 2;

$X^3$ is $C_1$–$C_6$ alkyl;

$R^2$ is hydroxy($C_1$–$C_4$ alkyl);

$R^3$ is $C_1$–$C_6$ alkenyl, —$CH_2$—$R^{3a}$, —C(O)—$R^{3b}$, —C(S)—$R^{3c}$, —C($CH_3$)$_2$C(O)$NH_2$ or a group of the formula:

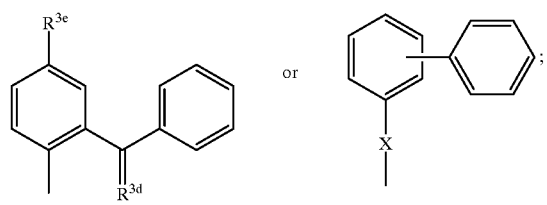

$R^{3a}$ is phenyl, p-fluorophenyl, pyridyl, piperidinyl, piperazinyl or morpholinyl;

$R^{3b}$ is piperidinyl, piperazinyl, morpholinyl, N-($C_1$–$C_4$ alkoxycarbonyl)piperidinyl, N-(trifluoromethyl)piperidinyl, halo($C_1$–$C_4$ alkoxy) or di($C_1$–$C_4$ alkyl)amino;

$R^{3c}$ is di($C_1$–$C_4$ alkyl)amino;

$R^{3d}$ is oxygen or hydroximino;

$R^{3e}$ is hydrogen, nitro or trifluoromethyl;

X is a bond;

$R^4$ is hydrogen, hydroxy, amino, =O, $C_2$–$C_6$ alkanoyloxy, =N—$R^5$ or —OSi ($CH_3$)$_2$;

$R^5$ is hydroxy, amino, di($C_1$–$C_4$ alkyl)amino, $C_1$–$C_4$ alkoxy, pyridylmethoxy, N-(methyl)piperazinyl or —O—$CH_2$—C(O)—$R^{5a}$;

$R^6$ is hydrogen, chloro, bromo, methyl or =O;

$R^7$ is hydrogen or methyl;

$R^8$ is hydroxy, chloro, methoxy, 4-methylpiperazinyl or —N($R^9$)—$R^{10}$;

$R^9$ is hydrogen;

$R^{10}$ is —$CH_2$—$R^{10a}$; and $R^{10a}$ is pyridyl;

or a pharmaceutically acceptable salt thereof.

Of these compounds, more preferred are those compounds of formula I where:

$R^0$ is hydrogen, hydroxy, $C_1$–$C_6$ alkoxy, —O—$(X^1)_i$—$X^2$, —$X^0$—O—C(O)—$C_1$–$C_4$ alkyl or —O—$R^3$;

$R^1$ is hydrogen, hydroxy, $C_1$–$C_6$ alkoxy or —O—$R^3$;

$X^0$ is a bond;

$X^1$ is an amino acid;

$X^2$ is hydrogen or an amino protecting group;

i is 1 or 2;

$R^3$ is $C_1$–$C_6$ alkenyl, —$CH_2$—$R^{3a}$ or —C(O)—$R^{3b}$;

$R^{3a}$ is p-fluorophenyl or pyridyl;

$R^{3b}$ is piperidinyl;

$R^4$ is hydrogen, hydroxy, =O or =N—$R^5$;

$R^5$ is hydroxy, dimethylamino or N-(methyl)piperazinyl;

$R^6$ is hydrogen, bromo or =O;

$R^7$ is methyl; and $R^8$ is methoxy;

or a pharmaceutically acceptable salt thereof.

Of these compounds, even more preferred are those compounds of formula I where:

$R^0$ is hydrogen, hydroxy, $C_1$–$C_4$ alkoxy, —O—$(X^1)_i$—$X^2$, —O—C(O)methyl or —O—$R^3$;

$R^1$ is hydrogen, hydroxy, $C_1$–$C_4$ alkoxy or —O—$R^3$;

$X^1$ is glycine, alanine or valine;

$X^2$ is hydrogen, t-butoxycarbonyl or benzyloxycarbonyl;

$R^4$ is =O or =N—$R^5$;

$R^5$ is hydroxy;

$R^6$ is hydrogen;

or a pharmaceutically acceptable salt thereof.

The compounds of formula I may be prepared according to procedures known in the art. For example, the following Reaction Schemes may be used, alone or in combination to provide the desired compounds. Once a reaction is complete, the intermediate compound may be isolated by procedures well-known in the art, for example, the compound may be crystallized and then collected by filtration, or the reaction solvent may be removed by extraction, evaporation or decantation. The intermediate compound may be further purified, if desired, by common techniques such as crystallization or chromatography over solid supports such as silica gel or alumina, before carrying out the next step of the reaction scheme.

The compounds of formula I where $R^4$ is =O or =N—R may be prepared according to the procedures shown below in Reaction Scheme I.

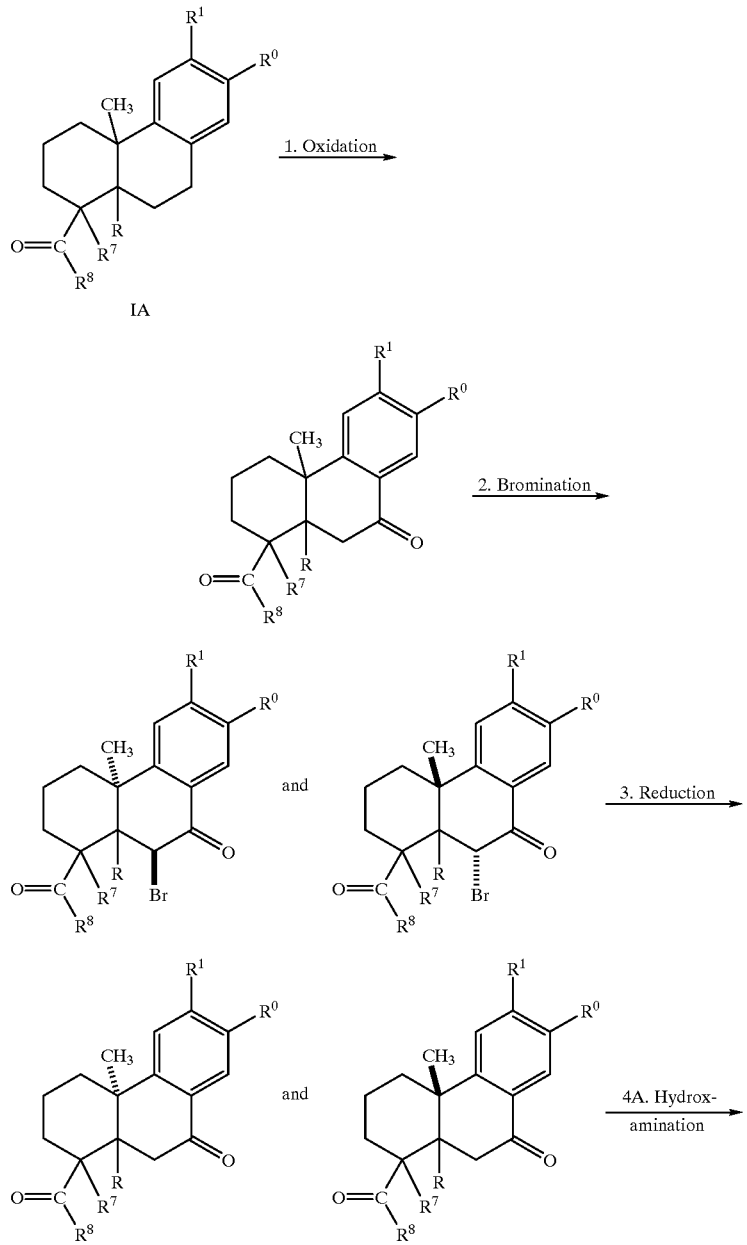

-continued

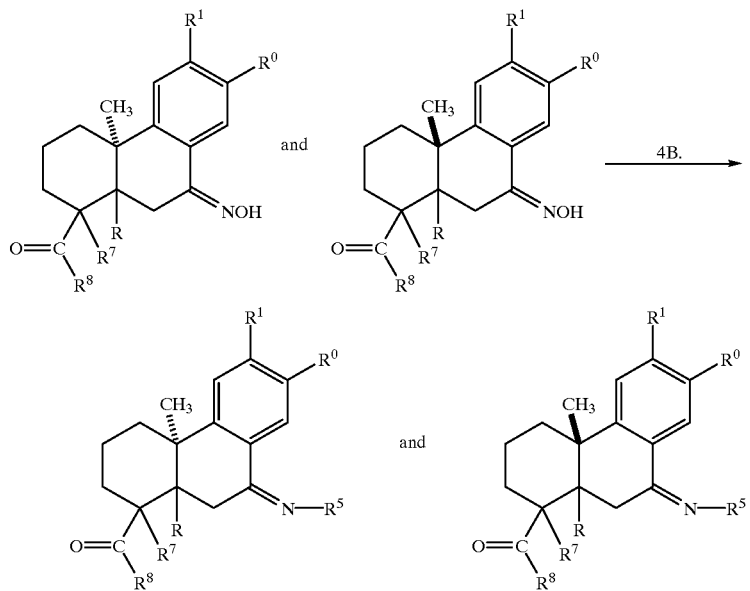

where Reactions I.4A and 4B represent alternative reactions that follow Reaction I.3.

Reaction scheme I is accomplished by carrying out reactions 1–4 is sequential order. Reaction I.1 is carried out by oxidizing a compound of formula IA, for example, by reaction with chromium trioxide in an acetic acid/water mixture, to provide the corresponding ketone. The chromium trioxide is generally employed in an amount ranging from equimolar proportions to about a 4 molar excess relative to the compound of formula IA, preferably in about a 2–4 molar excess. The acetic acid/water mixture is generally a 10:1 to a 2:1 mixture of acetic acid to water, preferably about 4:1. The reaction is generally substantially complete after about 1 to 10 hours when conducted at a temperature of from about 23° C. to about 60° C. The reaction is preferably conducted at a temperature of from about 23° C. to about 30° C. for about 5 to 10 hours.

In Reaction I.2, the ketone obtained from Reaction I.1 is reacted with bromine in a suitable solvent such as diethyl ether, tetrahydrofuran or dimethoxyethane, to provide a mixture of bromoketones which are then separated using standard separation techniques such as chromatography. These isomerically pure bromoketones are then used to prepare various isomerically pure compounds of formula I. The bromine is generally employed in an amount ranging from about equimolar proportions to about a 2 molar excess relative to the ketone reactant, preferably in about a 1–1.5 molar excess. Solvent choice is not critical so long as the solvent employed is inert to the ongoing reaction and the reactants are sufficiently solubilized to effect the desired reaction. The reaction is generally substantially complete after about 1 to 3 hours when conducted at a temperature of from about 23° C. to about 30° C. The reaction is preferably conducted at room temperature for about 1 to 1.5 hours.

Alternatively, the ketone obtained from Reaction I.1 is reacted with a silylating agent in the presence of a base in a suitable solvent such as methylene chloride, diethyl ether or tetrahydrofuran to provide the corresponding silylated enol ether. Preferred bases include 2,6-lutidine and collidine. A preferred silylating agent is t-butyldimethylsilyl trifluoromethanesulfonate. The silylating agent is generally employed in an amount ranging from about equimolar proportions to about a 2 molar excess relative to the ketone reactant, preferably in about a 1–1.5 molar excess. Solvent choice is not critical so long as the solvent employed is inert to the ongoing reaction and the reactants are sufficiently solubilized to effect the desired reaction. The reaction is generally substantially complete after about 30 minutes to 2 hours when conducted at a temperature of from about 0° C. to about 50° C. The reaction is preferably conducted at a temperature of from about 10° C. to about 25° C. for about 30 minutes to about 1 hour.

The silylated enol ether is then reacted with bromine substantially as described above with the exception that the reaction is carried out in the presence of acetic acid. Typical solvents suitable for use in this reaction include any organic solvent such as methylene chloride, diethyl ether or tetrahydrofuran. Solvent choice is not critical so long as the solvent employed is inert to the ongoing reaction and the reactants are sufficiently solubilized to effect the desired reaction.

In Reaction I.3, the bromoketone is reduced, for example by reaction with zinc dust and sodium acetate in glacial acetic acid, to provide the corresponding ketones. The zinc is generally employed in an amount ranging from about equimolar proportions to about a 4 molar excess relative to the ketone reactant, preferably in about a 1.5–3 molar excess. The sodium acetate is generally employed in an amount ranging from about 0.6 molar equivalents to about 1.2 molar equivalents relative to the ketone reactant. The reaction is generally substantially complete after about 1 to 10 hours when conducted at a temperature of from about 60° C. to the reflux temperature of the mixture. The reaction is preferably conducted at reflux temperature for about 1 to 2 hours.

Alternatively, hydroxylamine hydrochloride is reacted with sodium acetate in a suitable solvent such as ethanol. The sodium acetate is generally employed in an amount ranging from about 1.1 molar equivalents to about a 50 molar excess relative to the hydroxylamine. The reaction is generally substantially complete after about 1 to 72 hours when conducted at a temperature of from about 25° C. to about 80° C. The reaction is preferably conducted at a temperature in the range of from about 25° C. to about 30° C. for about 5 to 24 hours.

In Reaction I.4A, the ketone obtained from Reaction I.3 is reacted with hydroxylamine hydrochloride in a mixture of methanol, water and acetic acid to provide the desired oxime compound. The hydroxylamine hydrochloride is generally employed in an amount ranging from about equimolar proportions to about a 4 molar excess relative to the ketone reactant, preferably in about a 1.3–3 molar excess. The ratio of methanol to water to acetic acid is generally 10–20:1:0.1, preferably 15:1:0.1. The reaction is generally substantially complete after about 1 hour to about 2 days when conducted at a temperature of from about 40° C. to the reflux temperature of the mixture. The reaction is preferably conducted at reflux temperature for about 1 to 6 hours.

In Reaction I.4B, the ketone obtained from Reaction I.3 is reacted with an hydrazine hydrochloride such as 1-amino-4-methylpiperazine, 1,1-dimethylhydrazine or hydrazine in the presence of a base in an inert solvent at a temperature of from about 25° C. to 80° C. for 2 to 24 hours. Typical bases include sodium acetate, potassium hydroxide, triethylamine and the like. Suitable solvents include ethanol, isopropanol and dimethylformamide. Solvent choice is not critical so long as the solvent employed is inert to the ongoing reaction and the reactants are sufficiently solubilized to effect the desired reaction.

The phenyl moiety of the compounds of formula I prepared above may be substituted according to Reaction Scheme II, as follows.

Reaction Scheme II

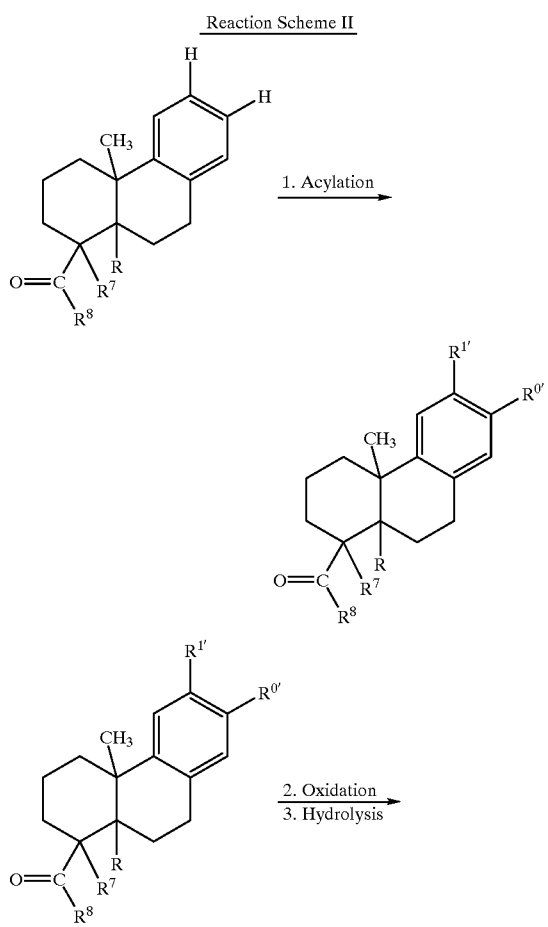

-continued

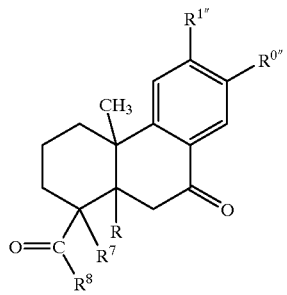

where $R^{0'}$ and $R^{1'}$ are independently hydrogen or —C(O)CH$_3$; and $R^{0''}$ and $R^{1''}$ are independently hydrogen or hydroxy.

In Reaction II.1, the compound of formula I where $R^0$ and $R^1$ are each hydrogen is subjected to a Friedel-Crafts acylation by reacting the compound of formula I with an acid halide, in the presence of a catalyst in an inert solvent such as carbon disulfide. The acid halide is generally employed in an amount ranging from about equimolar proportions to about a 1.5 molar excess relative to the compound of formula I, preferably in about a 1.1–1.3 molar excess. Preferred acid halides include acetyl chloride, acetyl bromide or the like. Preferred catalysts include aluminum trichloride, aluminum tribromide or the like. Solvent choice is not critical so long as the solvent employed is inert to the ongoing reaction and the reactants are sufficiently solubilized to effect the desired reaction. The reaction is generally substantially complete after about 1 to 10 hours when conducted at a temperature of from about 50° C. to the reflux temperature of the mixture. The reaction is preferably conducted at reflux temperature for about 1 to 2 hours.

In Reaction II.2, the acylated compound of formula I obtained from Reaction II.1 is oxidized to provide the corresponding phenol in a two step reaction. First, the acyl moiety is reacted with a peracid in the presence of an acid catalyst in an inert solvent such as dimethoxyethane to provide the corresponding ester with is then reacted with sodium bicarbonate in an alcohol/water mixture to provide the desired phenol.

The peracid is generally employed in an amount ranging from about equimolar proportions to about a 2 molar excess relative to the acyl moiety, preferably in about a 1–1.3 molar excess. The amount of catalyst typically employed is in the range of 0.005–0.04 equivalents relative to the acyl moiety. A preferred peracid is metachloro-peroxybenzoic acid. A preferred catalyst is p-toluenesulfonic acid. Solvent choice is not critical so long as the solvent employed is inert to the ongoing reaction and the reactants are sufficiently solubilized to effect the desired reaction. The reaction is generally substantially complete after about 1 to 10 hours when conducted at a temperature of from about 50° C. to the reflux temperature of the mixture. The reaction is preferably conducted at reflux temperature for about 1 to 3 hours.

The resultant ester is typically refluxed with a base in a methanol/water mixture for about 1 to 7 hours to provide the desired phenol compound. Preferred bases include sodium bicarbonate, sodium carbonate, sodium hydroxide or potassium hydroxide or the like. The base is generally employed in an excess, for example from about a 1 molar excess to about a 6 molar excess relative to the ester moiety, preferably in about a 2–5 molar excess.

The phenol compounds obtained from Reaction Scheme II may be used to prepare various substituted compounds of formula I, as described below.

For example, the hydroxy moiety may be alkylated by reacting the phenol compound with a suitable alkylating agent in the presence of a base in an inert solvent. Examples of bases include triethylamine, diisopropyl ethylamine, sodium hydride and potassium carbonate. Typical solvents include methylene chloride, tetrahydrofuran, dimethylformamide and the like. Solvent choice is not critical so long as the solvent employed is inert to the ongoing reaction and the reactants are sufficiently solubilized to effect the desired reaction. Suitable alkylating agents include iodomethane, allyl iodide, p-fluorophenyl bromide, 3-bromomethylpyridine and 2-fluorobenzophenone and the like. The reaction is generally substantially complete after about 1 to 20 hours when conducted at a temperature of from about 0° C. to 170° C. The reaction is preferably conducted at a temperature of from about 25° C. to about 80° C. for about 4 to 16 hours.

Alternatively, the hydroxy moiety may be alkylated by reacting the phenol with an alcohol in the presence of triphenylphosphine and a suitable activating agent in an inert solvent, such as tetrahydrofuran or ethylene glycol dimethyl ether. Examples of suitable activating agents include diethyl azodicarboxylate, dimethyl azodicarboxylate, diisopropyl azodicarboxylate and the like. Examples of alcohols include 3-pyridyl carbinol, N-t-butoxycarbonyl-3-piperidinemethanol and the like. The reaction is generally substantially complete after about 0.5 to 2 hours when conducted at a temperature of from about 0° C. to 85° C. The reaction is preferably conducted at a temperature of from about 25° C. to about 70° C. for about 30 minutes to 1 hour.

The hydroxy moiety may be converted to an ester or a carbonate by reacting the phenol with an acylating agent in the presence of a base in an inert solvent, such as methylene chloride, tetrahydrofuran or dimethylformamide. Typical bases include triethylamine, diisopropyl ethylamine, sodium hydride and the like. Typical acylating agents include N-(t-butoxycarbonyl)-4-chlorocarbonyl piperdine, 2,2,2-trichloroethyl chloroformate, N-(t-butoxycarbonyl)-hydroxybenzotriazole amino esters. The reaction is generally substantially complete after about 1 to 20 hours when conducted at a temperature of from about 0° C. to 60° C. The reaction is preferably conducted at a temperature of from about 10° C. to about 25° C. for about 1 to 5 hours.

The hydroxy moiety may be converted to the corresponding aniline in a three step reaction. First, the phenol is reacted with a suitably substituted amide such as 2-methyl-2-bromo-propanamide in the presence of a base such as sodium hydride or triethylamine in an inert solvent, such as dioxane or tetrahydrofuran at a temperature of 25° C. to 100° C. to provide the corresponding amido-ether. This amido-ether is then reacted with sodium hydride in an inert solvent such as dimethylformamide, 1,3-dimethyl-3,4,5,6-tetrahydro-2(1H)-pyrimidone or a mixture thereof at temperatures ranging from 25° C. to 145° C. to provide the rearranged amido-alcohol. Finally, the amido-alcohol is reacted with an acid, such as hydrochloric acid in dioxane at 50° C. to 100° C. to provide the desired aniline.

The aniline may be converted to the corresponding sulfonamide by reacting the aniline with a sulfonyl chloride such as methanesulfonyl chloride or isopropylsulfonyl chloride in the presence of a base, such as triethylamine, diisopropyl ethylamine or sodium hydride at a temperature of from about 0° C. to 50° C. in an inert solvent, such as methylene chloride, tetrahydrofuran or dimethylformamide.

The hydroxy moiety may be converted to a thiophenol in a three step reaction. First the phenol is reacted with a thio-carbamoyl (for example dimethylthiocarbamoyl chloride) in the presence of a base in an suitable solvent, such as water or dimethylformamide at a temperature ranging from 25° C. to 50° C. for 1 to 3 hours to provide the oxo-thiocarbamate. Typical bases include potassium hydroxide, triethylamine and the like. The oxo-thiocarbamate is converted to the corresponding thio-oxocarbamate compound by isolating and heating the neat solid to its melting point. Finally, the thio-oxocarbamate is reacted with a base, such as potassium hydroxide or sodium hydroxide in an alcoholic solvent, such as methanol or ethanol at a temperature of 20° C. to 80° C. for 20 minutes to 1 hour to provide the corresponding thiophenol.

The thiophenol may be converted to the corresponding sulfonamides by reacting the thiophenol with an oxidizing agent (for example, potassium nitrate) in an inert solvent such as acetonitrile, followed by the addition of a chlorinating agent (for example, sulfuryl chloride) at temperatures ranging from 0° C. to 25° C. to provide a mixture of sulfonyl chlorides which are separable using standard chromatographic techniques. These sulfonyl chlorides may be converted to the desired sulfonamides by reaction with an appropriately substituted amine such as ammonium hydroxide, methylamine, isopropylamine or benzylamine at a temperature of from about 0° C. to 40° C. in an inert solvent such tetrahydrofuran.

The hydroxy moiety may be converted to the corresponding amino esters by reacting the phenol with an amino protected amino acid in the presence of a coupling reagent and a catalyst in an inert solvent such as diethyl ether, tetrahydrofuran or methylene chloride. Preferred amino protecting groups include t-butoxycarbonyl or benzyloxycarbonyl. The amino reactant is generally employed in equimolar proportions to a slight excess (1.3 equivalents) relative to the phenol reactant in the presence of an equimolar quantity to a slight excess (1.5 equivalents) of the coupling reagent. Typical coupling agents include dicyclohexylcarbodiimide (DCC), 1-(3-dimethylaminopropyl)-3-ethylcarbodiimide, benzotriazol-1-yloxy-tris(dimethylamino)phosphonium hexafluorophosphate (BOP), N,N'-diethylcarbodiimide, carbonyldiimidazole, bis(2-oxo-3-oxazolidinyl)phosphinic chloride (BOP-Cl) or N-ethoxycarbonyl-2-ethoxy-1,2-dihydroquinoline (EEDQ) and the like. Preferred coupling agents include DCC and BOP. Typical catalysts include DMAP and 4-pyrrolopyridine. The reaction is substantially complete in 1 to 10 hours when carried out at a temperature of from about –30° C. to about 35° C., preferably from about 0° C. to about 25° C.

The starting materials used in the procedures detailed above may be obtained commercially or prepared according to procedures known in the art. For example, the compounds of formula IA:

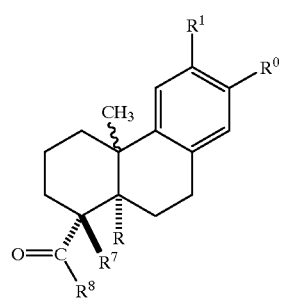

IA may be prepared substantially in accordance with the procedure detailed in Ohta and Ohmuri, Chem. Pharm. Bull.

(Tokyo), vol 5, page 91 (1957). The isomeric mix of compounds may be separated using standard separation techniques such as recrystallization or column chromatography or may be subjected to the bromination methodology described above in Reaction Scheme I. Preferably, these isomers are obtained using the bromination methodology described above in Reaction Scheme I.

The following Preparations and Examples further illustrate specific aspects of the present invention. It is to be understood, however, that these examples are included for illustrative purposes only and are not intended to limit the scope of the invention in any respect and should not be so construed.

EXAMPLE 1

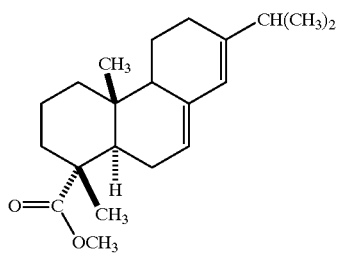

To a solution of NaOMe (prepared in situ from 2.6 g of sodium in 400 ml of anhydrous MeOH (0.108 mol), under $N_2$), was added 15.0 g (0.035 mol) of 70% abietic acid. After stirring the mixture for 10 minutes, 14.0 ml (0.22 mol) of iodomethane was added and the mixture was refluxed for 24 hours, cooled and concentrated in vacuo to provide a residue which was dissolved in 500 ml of EtOAc, washed sequentially with 500 ml of a saturated $NaHCO_3$ solution and a saturated sodium chloride solution (NaCl), dried over $Na_2SO_4$, filtered and concentrated in vacuo. The crude material was purified using flash chromatography (eluent of 2% EtOAc in hexanes).

Yield: 10.0 g of a dark yellow oil (90.4%). IR(CHCl$_3$): 2952, 1718 and 1251 cm$^{-1}$. $^1$H NMR (300 MHz, CDCl$_3$): δ 5.78 (s, 1H); 5.38 (brs, 1H); 3.66 (s, 3H); 2.17–2.30 (m, 3H); 1.68–2.16 (m, 8H); 1.50–1.65 (m, 2H); 1.26 (s, 3H); 1.24 (m, 2H); 1.02 (d, J=2.6 Hz, 3H); 1.00 (d, J=2.6 Hz, 3H) and 0.83 (s, 3H). MS(FD): m/e 316(M+). Elemental Analysis for $C_{21}H_{32}O_2$: Calcd: C, 79.70; H, 10.19; Found: C, 79.49; H, 9.94.

EXAMPLE 2

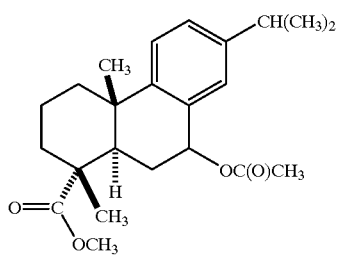

To a mixture of 5.0 g (15.8 mmol) of the compound in Example 1 in 100 ml of acetic anhydride, was added 2.5 g (22.5 mmol) of selenium (IV) oxide, under $N_2$. The reaction mixture was warmed to 70° C., stirred for 16 hours, cooled, filtered and then diluted to 500 ml with $CH_2Cl_2$. The resulting layers were separated and the organic layer was washed with 500 ml of NaCl, dried over $Na_2SO_4$, filtered and then concentrated in vacuo to provide a dark yellow solid. This solid was purified using flash chromatography (eluent of 5% EtOAc in hexanes) to provide two major fractions.

The first fraction was concentrated to provide 537 mg of an oil. This oil was hydrogenated with 135 mg of 5% Pd/C in 25 ml of MeOH (8 hours, room temperature, 6.0 psi). The reaction mixture was filtered and the filtrate concentrated in vacuo. The crude material was purified using flash chromatography (eluent of 2% EtOAc in hexanes) to provide the compound of Example 3 (400 mg of a clear oil (75%) m.p. 50° C.). The second fraction was concentrated in vacuo to provide the compound.

Yield: 2.8 g of a light yellow solid (47%). m.p. 165–167° C. IR (KBr): 2956, 1722 and 1251 cm$^{-1}$. $^1$H NMR (300 MHz, CDCl$_3$): δ 7.23 (m, 2H); 7.04 (d, J=1.8 Hz, 1H); 5.90 (m, 1H); 3.64 (s, 3H); 2.86 (m, 1H); 2.60 (dd, J=1.5,11.0 Hz, 1H); 2.31 (d, J=12.1 Hz, 1H); 2.08 (s, 3H); 2.07 (m, 1H); 1.60–1.80 (m, 6H); 1.26 (s, 3H); 1.24 (s, 3H); 1.22 (s, 3H) and 1.19 (s, 3H). MS(FD): m/e 372 (M+). Elemental Analysis for $C_{23}H_{32}O_4$: Calcd: C, 74.16; H, 8.66; Found: C, 74.44; H, 8.71.

EXAMPLE 3

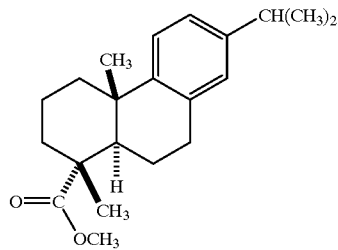

To a mixture of 23.6 g (0.063 mmol) of the compound in Example 2 in 1500 ml of MeOH, was added 5.8 g of 10% Pd/C and 5.8 g (0.030 mmol) of p-toluenesulfonic acid monohydrate. The reaction mixture was reacted for 16 hours at room temperature, 60 psi, filtered and then concentrated in vacuo to provide a residue. This residue was dissolved in 700 ml of EtOAc, washed sequentially with 700 ml of saturated $NaHCO_3$ and NaCl solutions, dried over $Na_2SO_4$, filtered and then concentrated in vacuo.

Yield: 19.3 g (97.5%) of an oil. IR (CHCl$_3$): 2955, 1718 and 1254 cm$^{-1}$. $^1$H NMR (300 MHz, CDCl$_3$): δ 7.16 (d, J=8 Hz, 1H); 7.00 (d, J=8 Hz, 1H); 6.88 (s, 1H); 3.66 (s, 3H); 2.80–2.90 (m, 3H); 2.23–2.32 (m, 2H); 1.35–1.90 (m, 7H); 1.28 (s, 3H); 1.24 (s, 3H) and 1.21 (s, 6H). MS(FD): m/e 314(M+). Elemental Analysis for $C_{21}H_{30}O_2$: Calcd: C, 80.21; H, 9.62 Found: C, 80.34; H, 9.73

EXAMPLE 4

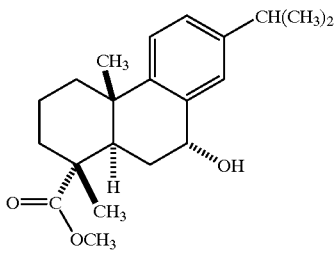

To a suspension of 185 mg (0.50 mmol) of the compound of Example 2 in 10 ml of MeOH, was added 5 ml (0.50 mmol) of 0.1N NaOH. The reaction mixture was refluxed for 2 hours, cooled and partitioned between 50 ml of EtOAc and 50 ml of 0.2N HCl. The resulting layers were separated and the organic layer was washed with 50 ml of a saturated NaCl solution, dried over $Na_2SO_4$, filtered and then concentrated in vacuo to provide a yellow oil. This oil was purified using flash chromatography (eluent of 10% EtOAc in hexanes).

Yield: 158 mg of a clear oil (96%). m.p. 105–107° C. IR (KBr): 2957, 3500 and 1719 cm$^{-1}$. $^1$H NMR (300 MHz, CDCl$_3$): δ 7.20 (m, 3H); 4.75 (t, J=4.8 Hz, 1H); 3.69 (s, 3H); 2.88 (m, 1H); 2.50 (dd, J=1.8,13.2 Hz, 1H); 2.30 (brd, J=12.1 Hz, 1H); 2.06–2.17 (m, 1H); 1.98 (d, J=7.0 Hz, 1H); 1.69–1.84 (m, 4H); 1.55 (m, 2H); 1.29 (s, 3H); 1.25 (s, 3H); 1.23 (s, 3H) and 1.17 (s, 3H). MS(FD): m/e 330(M+).

EXAMPLE 5

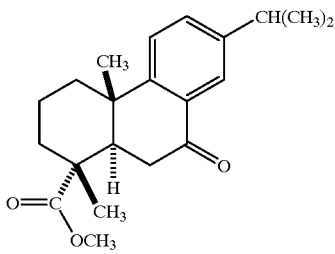

To a solution of 112 mg (0.30 mmol) of the compound of Example 4 in 4 ml of glacial AcOH and 1 ml of $H_2O$, was added 10 mg (1.0 mmol) of chromium trioxide. The reaction mixture was stirred at room temperature for 1 hour and then partitioned between 50 ml of EtOAc and 50 ml of a saturated NaCl solution. The resultant layers were separated and the organic layer was dried over $Na_2SO_4$, filtered and then concentrated in vacuo to provide a dark oil which was purified using flash chromatography (eluent of 5% EtOAc in hexanes) to provide an oil which solidified on standing.

Yield: 100 mg (90%). IR (CHCl$_3$): 2965, 1722, 1675 and 1253 cm$^{-1}$. $^1$H NMR (300 MHz, CDCl$_3$): δ 7.88 (d, J=1.8 Hz, 1H); 7.42 (dd, J=1.8,8.1 Hz, 1H); 7.30 (d, J=8.1 Hz, 1H); 3.66 (s, 3H); 2.86–2.98 (m, 1H); 2.66–2.76 (m, 2H); 2.28–2.40 (m, 2H); 1.60–1.90 (m, 5H); 1.35 (s, 3H); 1.26 (s, 6H) and 1.24 (s, 3H). MS(FD): m/e 329(M+). Elemental Analysis for $C_{21}H_{28}O_3$: Calcd: C, 76.79; H, 8.59; Found: C, 76.52; H, 8.53.

EXAMPLE 6

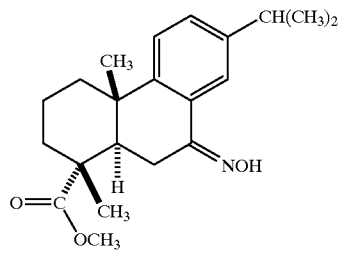

A mixture containing 118 mg (0.36 mmol) of the compound of Example 5, 40 mg (0.58 mmol) of hydroxylamine hydrochloride, 40 mg (0.48 mmol) of NaHCO$_3$, 1 drop of glacial AcOH, 1.0 ml of $H_2O$ and 15 ml of MeOH was refluxed with a Dean-Stark trap for 5 hours. The reaction mixture was concentrated in vacuo to provide a residue. This residue was partitioned between $H_2O$ and $CH_2Cl_2$ and the organic layer was dried over $Na_2SO_4$, filtered and concentrated in vacuo. The crude material was purified using flash chromatography.

Yield: 120 mg (97%). IR(CHCl$_3$): 3582, 2962, 1721 and 1261 cm$^{-1}$. $^1$H NMR (300 MHz, CDCl$_3$): δ 7.71 (s, 1H); 7.43 (s, 1H); 7.21 (s, 2H); 3.66 (s, 3H); 2.85–2.95 (m,1H); 2.67 (m, 2H); 2.26–2.37 (m, 2H); 1.75 (m, 5H); 1.38 (s, 3H); 1.26 (s, 3H); 1.24 (s, 3H); 1.13 (s, 3H); MS(FD) m/e 343(M+).

EXAMPLE 7

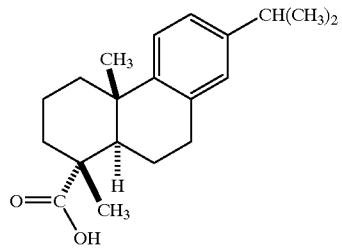

A mixture of 500 mg (1.59 mmol) of the compound of Example 3, 1.0 g (17.8 mmol) of KOH and 20 ml of n-butyl alcohol was refluxed for 16 hours, under $N_2$. After cooling, the mixture was acidified with 5N HCl and concentrated in vacuo to provide a residue. This residue was suspended in 50 ml of $H_2O$ and filtered. The resulting solid was dissolved in 50 ml of MeOH, filtered and the filtrate was concentrated in vacuo.

Yield: 330 mg of a foam (69%). m.p. 143–145° C. IR (KBr): 2958, 1695 and 1279 cm$^{-1}$. $^1$H NMR (300 MHz, CDCl$_3$): δ7.25 (d, J=3 Hz, 1H); 7.17 (d, J=8 Hz, 1H); 7.00 (dd, J=3.9 Hz, 1H); 6.89 (brs, 1H); 2.80–3.00 (m, 3H); 2.20–2.40 (m, 2H); 1.65–1.96 (m, 5H); 1.43–1.60 (m, 2H); 1.29 (s, 3H); 1.24 (s, 3H); 1.22 (s, 3H); 1.21 (s, 3H); MS(FD) m/e 301(M+). Elemental Analysis for $C_{20}H_{28}O_2 \cdot 0.5H_2O$: Calcd: C, 79.01; H, 9.47; Found: C, 79.19; H, 9.52.

EXAMPLE 8

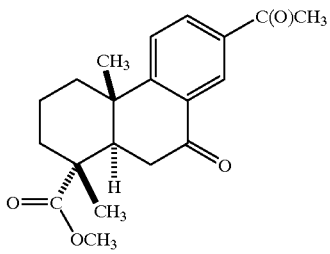

To a cold (0° C.) solution of 8.0 g (25.0 mmol) of the compound of Example 3 in 50 ml of acetic anhydride and 38 ml of AcOH, was added 11.0 g (0.11 mmol) of chromium trioxide slowly, under $N_2$. The reaction mixture was partitioned between EtOAc and brine and the organic layer was dried over $Na_2SO_4$, filtered and concentrated to provide a yellow oil. This oil was purified using flash chromatography ($SiO_2$, eluent of 10% EtOAc in hexanes) to provide a solid which was filtered with the aid of hexanes.

Yield: 2.5 g (30.5%). m.p. 144–145° C. IR (KBr): 2951, 1725 and 1680 cm$^{-1}$. $^1$H NMR (300 MHz, CDCl$_3$): δ 8.55 (d, J=2 Hz, 1H); 8.17 (dd, J=2,8 Hz, 1H); 7.50 (d, J=8 Hz, 1H); 3.66 (s, 3H); 2.75 (m, 2H); 2.64 (s, 3H); 2.37–2.50 (m, 2H); 1.60–1.90 (m, 5H); 1.37 (s, 3H) and 1.29 (s, 3H). MS(FD): m/e 328 (M+). Elemental Analysis for $C_{20}H_{24}O_4$: Calcd: C, 73.15; H, 7.37; Found: C, 72.86; H, 7.42.

EXAMPLE 9

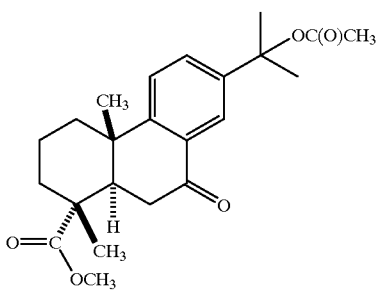

The compound was isolated from the reaction mixture described in Example 8.

Yield: 4.2 g of a white solid (43.5%). m.p. 130–133° C. IR (KBr): 2934, 1734, 1720 and 1680 cm$^{-1}$. $^1$H NMR (300 MHz, CDCl$_3$): δ 7.98 (d, J=2 Hz, 1H); 7.54 (dd, J=2,8 Hz, 1H); 7.33 (d, J=8 Hz, 1H); 3.66 (s, 3H); 2.75 (m, 2H); 2.30–2.42 (m, 2H); 2.2 (m, 1H); 2.04 (s, 3H); 2.00–2.10 (m, 1H); 1.70–1.90 (m, 3H); 1.76 (s, 6H); 1.35 (s, 3H) and 1.26 (s, 3H). MS(FD): m/e 386 (M+). Elemental Analysis for $C_{23}H_{30}O_5$: Calcd: C, 71.48; H, 7.82; Found: C, 71.75; H, 8.03.

EXAMPLE 10

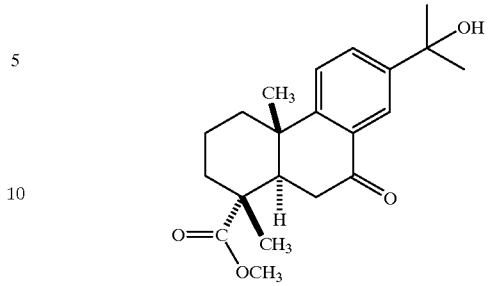

To a solution of 4.14 g (10.7 mmol) of the compound of Example 9 in 40 ml of MeOH, was added 13.4 ml (13.4 mmol) of 1N NaOH. The reaction mixture was refluxed for 2.5 hours, cooled and then partitioned between 200 ml of 0.2N HCl and 200 ml of EtOAc. The resultant layers were separated and the organic layer was washed with 200 ml of brine, dried over $Na_2SO_4$, filtered and then concentrated in vacuo to provide a dark yellow oil. This oil was purified using flash chromatography ($SiO_2$, eluent of 15% EtOAc in hexanes).

Yield: 2.9 g of a white foam (80%). m.p. 57–60° C. IR(KBr): 3444, 2936, 1727 and 1682 cm$^{-1}$. $^1$H NMR (300 MHz, CDCl$_3$): δ 8.06 (d, J=2.2 Hz, 1H); 7.74 (dd, J=2.2,8.5 Hz, 1H); 7.36 (d, J=8.5 Hz, 1H); 3.66 (s, 3H); 2.70 (m, 2H); 2.40 (m, 2H); 1.60–1.90 (m, 6H); 1.60 (s, 3H); 1.55 (s, 3H); 1.35 (s, 3H) and 1.27 (s, 3H). MS(FD): m/e 344(M+). Elemental Analysis for $C_{21}H_{28}O_4$: Calcd: C, 73.23; H, 8.19; Found: C, 73.50; H, 8.46.

EXAMPLE 11

A mixture of 500 mg (1.52 mmol) of the compound of Example 8, 620 mg (1.80 mmol) of 50% m-chloroperbenzoic acid, 5.0 mg (0.03 mmol) of p-toluene sulfonic acid monohydrate and 5 ml of 1,2-dichloroethane was refluxed for 4 hours and then stirred overnight at room temperature. The mixture was diluted with 25 ml of EtOAc and washed sequentially with 25 ml of 10% potassium iodide, 10% sodium thiosulfate, saturated NaHCO$_3$ and brine, dried over Na$_2$SO$_4$, filtered and then concentrated in vacuo. The crude material was purified by radial chromatography (eluent of 25% Et$_2$O in hexanes)

Yield: 30 mg (6%). IR(CHCl$_3$): 3020, 1723 and 1684 cm$^{-1}$. $^1$H NMR (300 MHz, CDCl$_3$): δ 7.69 (d, J=3 Hz, 1H); 7.39 (d, J=9 Hz, 1H); 7.24 (d, J=3 Hz, 1H); 3.67 (s, 3H); 2.84 (m, 2H); 2.25–2.42 (m, 2H); 2.31 (s, 3H); 1.60–1.90 (m, 5H); 1.35 (s, 3H) and 1.28 (s, 3H). MS(FD): m/e 344(M+). Elemental Analysis for $C_{20}H_{24}O_5$: Calcd: C, 69.75; H, 7.02; Found: C, 69.77; H, 6.92.

EXAMPLE 12

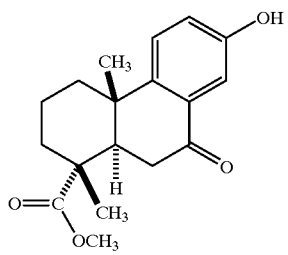

The compound was prepared substantially in accordance with the procedure detailed in Matsumoto et al., Bull. Chem. Soc. Jpn., vol. 61, pages 723–727 (1988), using the compound of Example 8.

Yield: 42%. IR(CHCl$_3$): 3389, 2948, 1725, 1670, 1606 cm$^{-1}$. $^1$H NMR (300 MHz, CDCl$_3$): δ 7.45 (d, J=3 Hz, 1H); 7.27 (d, J=9 Hz, 1H); 7.07 (dd, J=3,9 Hz, 1H); 5.20 (s, 1H); 3.66 (s, 3H); 2.65–2.80 (m, 2H); 2.27–2.42 (m, 2H); 1.60–1.90 (m, 5H);.1.34 (s, 3H) and 1.25 (s, 3H). MS(FD): m/e 302(M+). Elemental Analysis for C$_{18}$H$_{22}$O$_4$: Calcd: C, 71.50; H, 7.33; Found: C, 71.22; H, 7.19.

EXAMPLE 13

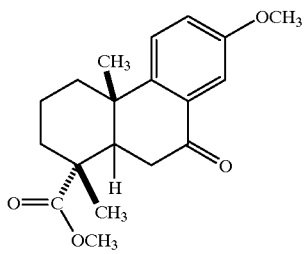

The compound was prepared substantially in accordance with the procedure detailed in Matsumoto et al., Bull. Chem. Soc. Jpn., vol. 61, 723–727 (1988), using the compound of Example 12.

Yield: 86%. IR(CHCl$_3$): 2941, 1722, 1677 and 1252 cm$^{-1}$. $^1$H NMR (300 MHz, CDCl$_3$): δ 7.48 (d, J=3 Hz, 1H); 7.29 (d, J=9 Hz, 1H); 7.11 (dd, J=3,9 Hz, 1H); 3.84 (s, 3H); 3.66 (s, 3H); 2.70 (m, 2H); 2.30–2.43 (m, 2H); 1.60–1.90 (m, 5H); 1.34 (s, 3H) and 1.25 (s, 3H). MS(FD): m/e 316(M+). Elemental Analysis for C$_{19}$H$_{24}$O$_4$: Calcd: C, 72.13; H, 7.65; Found: C, 72.16; H, 7.35.

EXAMPLE 14

A.

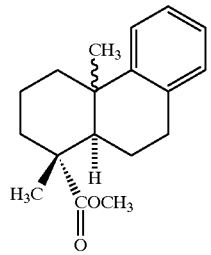

A mixture of 475 mg (1.5 mmol) of the compound of Example 3, 425 mg (3.19 mmol) of anhydrous aluminum chloride in 15 ml of toluene was stirred at room temperature for 2 hours, under N$_2$. The reaction mixture was partitioned between toluene and 1N HCl. The resultant layers were separated and the organic layer was washed with brine, dried over Na$_2$SO$_4$, filtered and concentrated in vacuo to provide an oil. This oil was purified using flash chromatography (SiO$_2$, eluent of 2% EtOAc in hexanes) to provide an oil which was crystallized from MeOH. $^1$H NMR (300 MHz, CDCl$_3$): δ 7.00–7.30 (m, 4H) ; 3.30 (s, 1.5H); 3.28 (s, 1.5H); 2.90 (m, 2H); 2.30 (m, 2H); 2.00 (m, 1H); 1.40–1.80 (m, 6H); 1.30 (s, 1.5H); 1.22 (s, 3H) and 1.10 (s, 1.5H).

B.

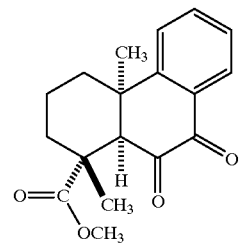

A solution of 285 mg (2.8 mmol) of chromium trioxide in 4 ml of glacial AcOH and 1 ml of H$_2$O was added dropwise to a solution of 275 mg (1 mmol) of the compound of Example 14A in 5 ml of glacial AcOH. The reaction mixture was stirred at room temperature for 2 hours and then partitioned between EtOAc and brine (twice). The combined organic layers were dried over Na$_2$SO$_4$, filtered and then concentrated in vacuo to provide a yellow oil which was purified using flash chromatography (SiO$_2$, eluent of 5% EtOAc in hexanes).

Yield: 50 mg of a bright yellow solid (17%). m.p. 121–123° C. IR(CHCl$_3$): 3019, 2954, 1727, 1688 and 1248 cm$^{-1}$. $^1$H NMR (300 MHz, CDCl$_3$): δ 8.14 (d, J=8 Hz, 1H); 7.70 (7, J=7Hz, 1H); 7.47 (m, 2H); 3.73 (s, 3H); 3.39 (s, 1H); 2.64 (d, J=12Hz, 1H); 2.01–2.11 (m, 1H); 1.40–1.80 (m, 4H); 1.29 (s, 3H) and 0.69 (s, 3H). MS(FD): m/e 300(M+). Elemental Analysis for C$_{18}$H$_{20}$O$_4$: Calcd: C, 71.98; H, 6.71; Found: C, 72.10; H, 6.66.

C.

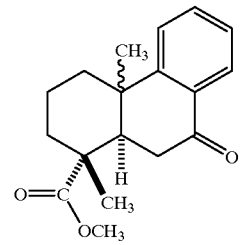

The compound was isolated Example 14B.

Yield: 136 mg of an oil (47.5%). $^1$H NMR (300 MHz, CDCl$_3$): δ 8.01 (m, 1H); 7.55 (m, 1H); 7.30 (m, 2H); 3.30 (s, 1.5H); 3.28 (s, 1.5H); 3.10 (dd, J=4,12 Hz, 0.5H): 2.70 (m, 1.5H); 2.40 (m, 2H); 1.40–1.90 (m, 5H); 1.30 (s, 1.5H); 1.28 (s, 1.5H); 1.23 (s, 1.5H); 0.65 (s, 1.5H).

EXAMPLE 15

A.

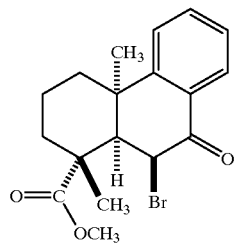

A solution of 0.9 ml (17 mmol) of bromine in 30 ml of anhydrous Et$_2$O was added to a solution of 3.8 g (13.3 mmol) of the compound of Example 14C in 200 ml of anhydrous Et$_2$O, dropwise. The reaction mixture was stirred at room temperature for 1 hour and then washed sequentially with H$_2$O, a saturated NaHCO$_3$ solution and 19% sodium thiosulfate, dried over Na$_2$SO$_4$, filtered and concentrated in vacuo to provide a residue. This residue was purified using flash chromatography (eluent of 3:2 CH$_2$Cl$_2$/hexanes).

Yield: 1.2 g of yellowish oil (25%). $^1$H NMR (300 MHz, CDCl$_3$): δ 8.00 (dd, J=2,5 Hz, 1H); 7.60 (dt, J=2,5 Hz, 1H); 7.40 (m, 2H); 4.60 (S, 1H); 3.78 (s, 3H); 3.25 (s, 1H) 2.50 (d, J=7 Hz, 1H); 1.60–1.90 (m, 5H); 1.60 (s 3H); 0.57 (s, 3H).

B.

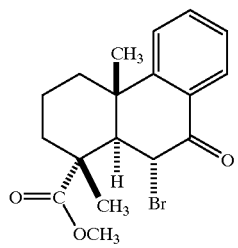

The compound was isolated from Example 15A.

Yield: 1.2 g of an oil (25%). $^1$H NMR (300 MHz, CDCl$_3$): δ 8.01 (d, J=6 Hz, 1H); 7.60 (m, 1H); 7.40 (m, 2H); 5.00 (d, J=9Hz, 1H); 3.65 (s, 3H); 3.23 (d, J=9 Hz, 1H); 2.60 (m, 1H); 2.38 (d, J=7 Hz, 1H); 1.80 (m, 4H); 1.52 (s, 3H) and 1.25 (s, 3H).

EXAMPLE 16

A.

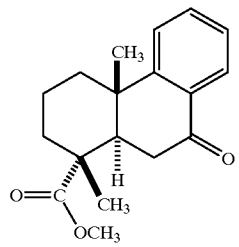

A mixture of 960 mg (2.6 mmol) of the compound of Example 15B, 4.0 g (61.2 mmol) of zinc dust, 2.0 g (24.4 mmol) of NaOAc and 50 ml of glacial AcOH was refluxed for 1 hour, under N$_2$. After cooling, the reaction mixture was filtered and the filtrate was partitioned between Et$_2$O and brine. The resultant layers were separated and the organic layer was dried over Na$_2$SO$_4$, filtered and then concentrated in vacuo. The crude material was purified using flash chromatography (SiO$_2$, eluent of 10% Et$_2$O in hexanes).

Yield: 500 mg of an oil (67.2%). IR(CHCl$_3$): 3028, 1722, 1679, 1258 cm$^{-1}$. $^1$H NMR (300 MHz, CDCl$_3$): δ 8.01 (d, J=8 Hz, 1H); 7.54 (7, 6 Hz, 1H); 7.29 (m, 2H); 3.67 (s, 3H); 2.74 (dd, J=3,7 Hz, 2H); 2.30–2.45 (m, 2H); 1.60–1.90 (m, 5H); 1.36 (s, 3H) and 1.28 (s, 3H). MS(FD): m/e 286(M+).

B.

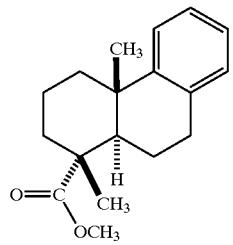

The compound was isolated from Example 16A.

Yield: 150 mg (21%).

EXAMPLE 17

A.

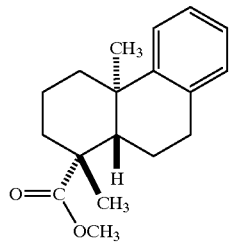

A solution of 1.54 g (5.66 mmol) of the compound of Example 14A and 1.5 g of 10% Pd/C in 150 ml of triethyleneglycol dimethyl ether was refluxed for 3 hours, under N$_2$. After cooling, the mixture was filtered and the filtrate was partitioned between EtOAc and brine (three times.). The resultant layers were separated and the combined organic layers were dried over Na$_2$SO$_4$, filtered and the concentrated in vacuo to provide 1.5 g of a residue. A fraction of this residue (300 mg) was purified by chromatotron (eluent of 2% CH$_2$Cl$_2$ in hexanes initially, followed by the addition to the mobile phase of 50 ml of CH$_2$Cl$_2$ after 200 ml elution, and finally 4 ml of EtOAc after 300 ml had eluted).

Yield: 29 mg 1H NMR (300 MHz, CDCl$_3$): δ 7.00–7.30 (m, 4H); 3.63 (s, 3H); 2.83 (m, 2H); 2.30 (m, 3H); 2.00 (m, 2H); 1.30–1.70 (m, 3H); 1.25 (s, 3H); 1.10 (m, 1H); 1.02 (s, 3H).

B. A mixture of

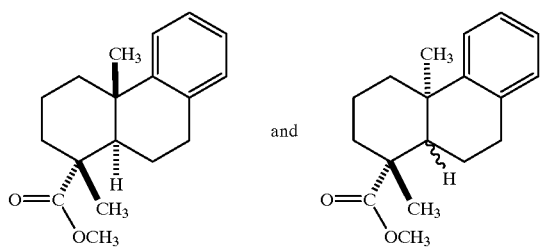

and

The compounds were isolated from Example 17A.
Yield: 216 mg.

EXAMPLE 18

A. A mixture of

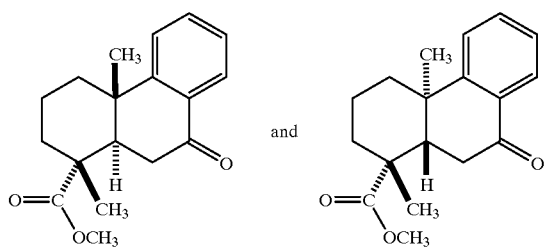

and

The compounds were prepared substantially in accordance with the procedure detailed in Example 14B, using a solution of 325 mg (1.2 mmol) of the unpurified residue from Example 17A in 5 ml of glacial AcOH The crude material was purified using flash chromatography (SiO$_2$, eluent of 15% Et$_2$O in hexanes).

Yield: 62 mg of an oil.

EXAMPLE 19

A.

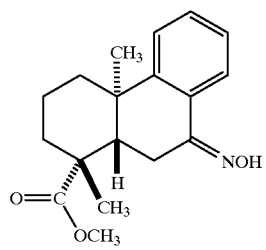

The compound was prepared substantially in accordance with the procedure detailed in Example 6, using a solution containing 140 mg (0.49 mmol) of the compounds of Example 18A in 10 ml of MeOH. The crude material was purified using flash chromatography (SiO$_2$, eluent of 20% Et$_2$O in hexanes).

Yield: 38 mg of a solid (26%). m.p. 139–141° C. IR(CHCl$_3$): 3584, 3020 and 1720 cm$^{-1}$. $^1$H NMR (300 MHz, CDCl$_3$): δ 7.92 (d, J=7.7 Hz, 1H); 7.56 (s, 1H); 7.30 (m, 2H); 7.20 (m, 1H); 3.72 (s, 3H); 3.44 (dd, J=4.0,18.4 Hz, 1H); 3.12 (dd, J=14.0,18.7 Hz, 1H); 2.35 (m, 2H); 2.03 (m, 1H); 1.50–1.80 (m, 3H); 1.32 (s, 3H); 1.10 (m, 1H) and 1.02 (s, 3H). MS(FD): m/e 301(M+). Elemental Analysis for C$_{18}$H$_{23}$NO$_3$: Calcd: C, 71.74; H, 7.69; N, 4.65; Found: C, 71.97; H, 7.77; N, 4.39.

B.

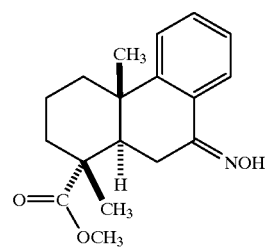

The compound was isolated from Example 19A.

Yield: 38 mg of a resin (26%). IR(CHCl$_3$): 3583, 3027, 2935, 1721 and 1263 cm$^{-1}$. $^1$H NMR (300 MHz, CDCl$_3$): δ 7.85 (d, J=8.1 Hz, 1H); 7.43 (s, 1H); 7.10–7.20 (m, 3H); 3.66 (s, 3H); 2.67 (d, J=8.8 Hz, 2H); 2.28–2.37 (m, 2H); 1.76 (m, 4H); 1.39 (s, 3H); 1.26 (m, 1H) and 1.14 (s, 3H). MS(FD): m/e 301(M+).

EXAMPLE 20

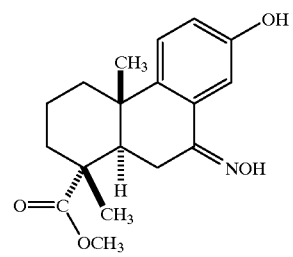

The compound was prepared substantially in accordance with the procedure detailed in Example 6, using the compound of Example 12.

IR(KBr): 3393, 2932, 1727 and 1702 cm$^{-1}$. $^1$H NMR (300 MHz, CDCl$_3$): δ 8.00 (brs, 1H); 7.29 (d, J=3 Hz, 1H); 7.16 (d, J=9 Hz, 1H); 6.85 (dd, J=3,9 Hz, 1H); 5.25 (brs, 1H); 3.68 (s, 3H); 2.65 (m, 2H); 2.20–2.40 (m, 2H); 1.55–2.04 (m, 5H); 1.40 (s, 3H) and 1.10 (s, 3H). MS(FD): m/e 318(M+). Elemental Analysis for C$_{18}$H$_{23}$O$_4$: Calcd: C, 68.12; H, 7.30; N, 4.41; Found: C, 67.95; H, 7.46; N, 4.12.

EXAMPLE 21

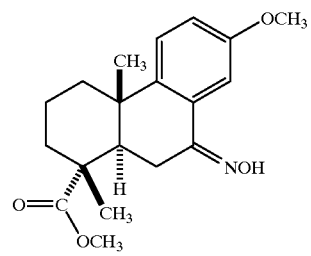

The compound was prepared substantially in accordance with the procedure detailed in Example 6, using the compound of Example 13.

Yield: 93%. IR(KBr): 3421, 2936, 1727 cm$^{-1}$. $^1$H NMR (300 MHz, CDCl$_3$): δ 7.37 (d, J=3 Hz, 1H); 7.29 (s, 1H); 6.92 (d, J=9 Hz, 1H); 6.91 (dd, J=3,9 Hz, 1H); 3.81 (s, 3H); 3.66 (s, 3H); 2.65 (m, 2H); 2.25–2.65 (m, 2H); 1.60–1.80

(m, 5H); 1.38 (s, 3H) and 1.11 (s, 3H). MS(FD): m/e 331(M+). Elemental Analysis for $C_{19}H_{25}NO_4$: Calcd: C, 68.86; H, 7.60; N, 4.23' Found: C, 69.10; H, 7.83; N, 4.23.

EXAMPLE 22

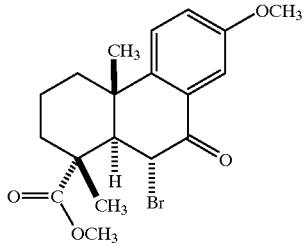

The compound was prepared substantially in accordance with the procedure detailed in Example 15A, using the compound of Example 13.

Yield: 74% m.p. 146–148° C. IR(KBr): 2900, 1725 and 1679 cm$^{-1}$. $^1$H NMR (300 MHz, CDCl$_3$): δ 7.46 (d, J=3 Hz, 1H); 7.28 (d, J=9 Hz, 1H); 7.14 (dd, J=3,9 Hz, 1H); 4.98 (d, J=13 Hz, 1H); 3.85 (s, 3H); 3.65 (s, 3H); 3.20 (d, J=13 Hz, 1H); 2.35 (m, 1H); 1.70–1.90 (m, 5H); 1.50 (s, 3H); 1.26 (s, 3H). MS(FD): m/e 397 (M+). Elemental Analysis for $C_{19}H_{23}BrO_4$: Calcd: C, 57.73; H, 5.86; Found: C, 57.78; H, 6.06.

EXAMPLE 23

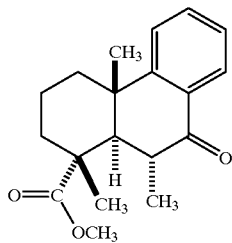

To a stirring solution of 70 mg (0.245 mmol) of the compound of Example 16A in 20 ml of anhydrous THF, was added 32 mg (0.80 mmol) of 60% NaH on mineral oil, under N$_2$. The resultant mixture was stirred 15 minutes followed by the addition of 0.15 ml (2.25 mmol) of iodomethane, via syringe. The reaction mixture was stirred for 3 hours, quenched by the dropwise addition of H$_2$O and then partitioned between Et$_2$O and H$_2$O. The resultant layers were separated and the organic layer was dried over Na$_2$SO$_4$, filtered and concentrated in vacuo to provide a residue which was purified by radial chromatography (eluent of 10% Et$_2$O in hexanes).

Yield: 16 mg of a clear oil (22%). IR(CHCl$_3$): 3692, 3022, 2950, 1724 and 1678 cm$^{-1}$. $^1$H NMR (300 MHz, CDCl$_3$): δ 7.95 (d, J=7.7 Hz, 1H); 7.54 (s, J=8.8 Hz, 1H); 7.25 (m, 2H); 3.63 (s, 3H); 2.80 (m, 2H); 2.39 (d, J=7.7 Hz, 1H); 1.70–2.05 (m, 5H); 1.43 (s, 3H); 1.28 (s, 3H) and 1.13 (d, J=6.2 Hz, 3H). MS(FD): m/e 300 (M+). Elemental Analysis for $C_{19}H_{24}O_3$: Calcd: C, 75.97; H, 8.05; Found: C, 75.80; H, 7.96.

EXAMPLE 24

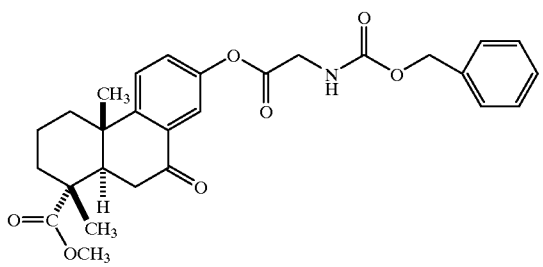

A mixture of 50 mg (0.165 mmol) of the compound of Example 12, 35 mg (0.165 mmol) of carbobenzyloxyglycine, 35 mg (0.170 mmol) of 1,3-dicyclohexylcarbodiimide (DCC), 2 mg (0.0165 mmol) of 4-dimethylaminopyridine in 25 ml of anhydrous Et$_2$O was stirred for 16 hours resulting in the formation of a solid. This solid was removed by filtration and the filtrate was washed sequentially with H$_2$O, a 5% AcOH solution and brine. The combined organic layers were dried over Na$_2$SO$_4$, filtered and then concentrated in vacuo to provide a resin. This resin was purified using flash chromatography (SiO$_2$, eluent of 20% Et$_2$O in hexanes).

Yield: 54 mg of a light yellow solid (66%). IR(KBr): 3330, 2934, 1779, 1725, 1685 cm$^{-1}$. $^1$H NMR (300 MHz, CDCl$_3$): δ 7.70 (s, 1H); 7.36 (m, 8H); 6.20 (s, 2H); 4.26 (d, J=6 Hz, 2H); 3.67 (s, 3H); 2.73 (dd, J=3,6 Hz, 2H); 2.40 (m, 2H); 1.50–2.00 (m, 5H); 1.35 (s, 3H); 1.28 and (s, 3H). MS(FD): m/e 494 (M+).

EXAMPLE 25

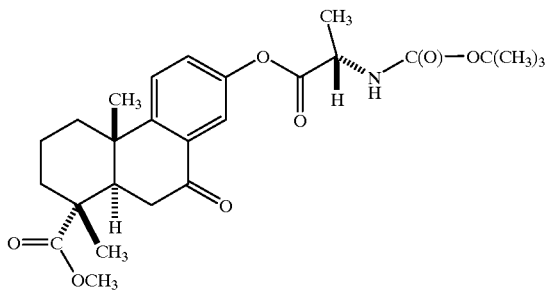

The compound was prepared substantially in accordance with the procedure detailed in Example 24, using the compound of Example 12 and N-t-butoxycarbonyl-L-alanine Yield: 96%. IR(CHCl$_3$): 3444, 2938, 1763, 1714 cm$^{-1}$. $^1$H NMR (300 MHz, CDCl$_3$,): δ 7.69 (d, J=2.6 Hz, 1H); 7.41 (d, J=8.5 Hz, 1H); 7.30 (d, J=2.6 Hz, 1H); 5.10 (brm, 1H); 4.55 (brm, 1H); 3.65 (s, 3H); 2.73 (dd, J=3.3, 6.6 Hz, 2H); 2.32–2.42 (m, 2H); 1.70–2.20 (m, 5H); 1.55 (d, J=7.0 Hz, 3H); 1.47 (s, 6H); 1.43 (s, 3H); 1.35 (s, 3H) and 1.28 (s, 3H). MS(FD): m/e 474 (M+).

EXAMPLE 26

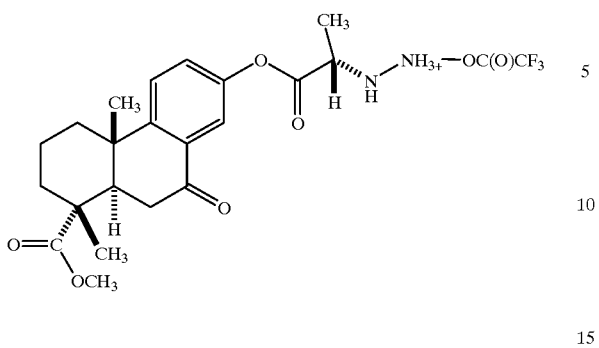

A mixture of 100 mg (0.21 mmol) of the compound of Example 25 in 2 ml of CH$_2$Cl$_2$ was added to 2 ml of a 1:1 CH$_2$Cl$_2$/CF$_3$COOH mixture. After stirring for 1 hour, the reaction mixture was concentrated in vacuo. The resultant residue was concentrated repetitively in Et$_2$O until a foam was obtained.

Yield: 85 mg (83%). IR(CHCl$_3$): 2941, 1715, 1711 and 1682 cm$^{-1}$. $^1$H NMR (300 MHz, CDCl$_3$): δ 7.65 (m, 2H); 7.41 (d, J=8.1 Hz, 1H); 4.30 (m, 1H); 3.62 (s, 3H); 2.63 (m, 2H); 2.25–2.40 (m, 2H); 1.60–1.90 (m, 5H); 1.34 (s, 3H) and 1.24 (s, 3H); 1.22 (d, J=7.0 Hz, 3H). MS(FD): m/e 374, free base (M+).

EXAMPLE 27

A.

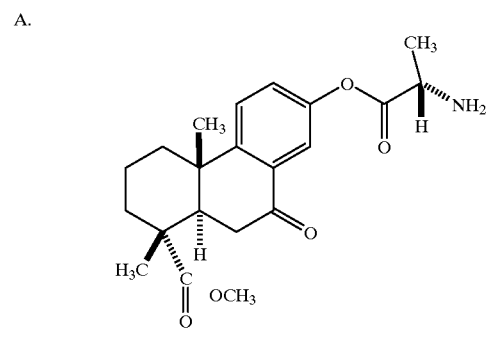

To a solution of 550 mg (1.0 mmol) of the compound of Example 25 in 10 ml of CH$_2$Cl$_2$, was added 3 ml (39 mmol) of CF$_3$COOH. After stirring for 1 hour, the reaction mixture was concentrated in vacuo to provide a foam. This foam was dissolved in 20 ml of CH$_2$Cl$_2$ followed by the addition of 0.17 ml (1.2 mmol) of Et$_3$N. The resultant layers were separated and the organic layer was washed with H$_2$O, dried over Na$_2$SO$_4$, filtered and concentrated in vacuo to provide a foam.

B.

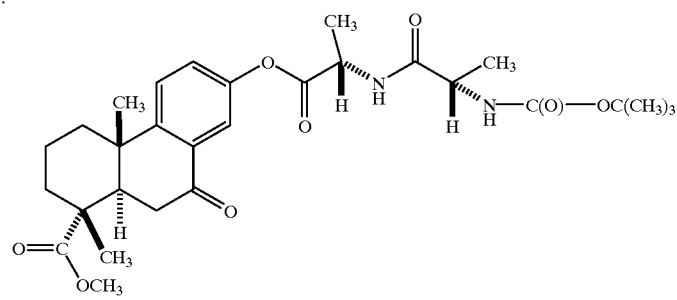

The compound was prepared substantially in accordance with the procedure detailed in Example 24, using the compound of Example 27A and 230 mg (1.2 mmol) of N-t-butyloxycarbonyl-L-alanine Yield: 255 mg (47%). IR(KBr) : 3334, 2938, 1770, 1725 and 1687 cm$^{-1}$. $^1$H NMR (300 MHz, CDCl$_3$): δ 7.69 (d, J=3 Hz, 1H); 7.41 (d, J=9 Hz, 1H); 7.29 (d, J=3 Hz, 1H); 6.70 (m, 1H); 5.00 (m, 1H); 4.80 (m, 1H); 4.20 (m, 1H); 3.67 (s, 3H); 2.73 (m, 2H); 2.36 (m, 2H); 1.60–1.90 (m, 5H); 1.58 (d, J=7 Hz, 3H); 1.45 (s, 9H); 1.38 (d, J=7 Hz, 3H); 1.35 (s, 3H) and 1.27 (s, 3H). MS(FD): m/e 544 (M+). Elemental Analysis for $C_{29}H_{40}N_2O_8 \cdot 0.75H_2O$: Calcd: C, 62.40; H, 7.43; N, 5.02; Found: C, 62.30; H, 7.24; N, 4.77.

EXAMPLE 28

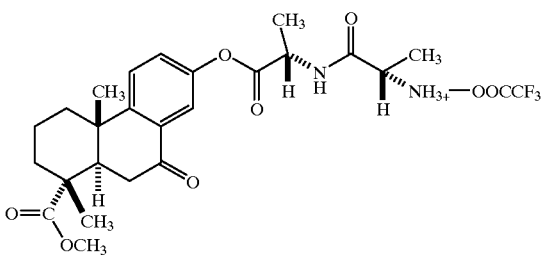

The compound was prepared substantially in accordance with the procedure detailed in Example 26, using the compound of Example 27B.

Yield: 95%. IR(KBr): 2950, 1770 and 1681 cm$^{-1}$. $^1$H NMR (300 MHz, CDCl$_3$): δ 8.17 (brs, 3H); 7.60 (s, 1H); 7.40 (d, J=2.6 Hz, 1H); 7.27 (m, 1H); 4.65 (brs, 1H); 4.40 (brs, 1H); 3.70 (d, J=2 Hz, 1H); 3.62 (s, 3H); 2.70 (m, 7H); 2.35 (m, 2H); 1.50–1.85 (m, 6H); 1.32 (s, 3H) and 1.23 (s, 3H). MS(FD): m/e 445 free base (M+).

EXAMPLE 29

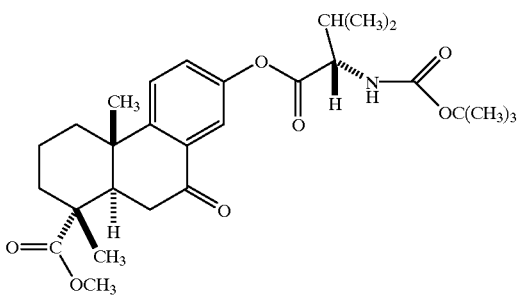

The compound was prepared substantially in accordance with the procedure detailed in Example 24, using the compound of Example 12 and N-t-butoxycarbonyl-L-valine.

Yield: 47%. IR(KBr): 3377, 2969, 1766, 1724 and 1688 cm$^{-1}$. $^1$H NMR (300 MHz, CDCl$_3$): δ 7.68 (d, J=2.6 Hz, 1H); 7.41 (d, J=8.8 Hz, 1H); 7.29 (d, J=2.6 Hz, 1H); 5.06 (brm, 1H); 4.45 (brm, 1H); 3.65 (s, 3H); 2.74 (dd, J=3.3,7.0 Hz, 2H); 2.30–2.43 (m, 1H); 1.70–1.90 (m, 6H); 1.48 (s, 9H); 1.35 (s, 3H); 1.28 (s, 3H); 1.09 (d, J=6.6 Hz, 3H); 1.02 (d, J=7.0 Hz, 3H). MS(FD): m/e 502 (M+). Elemental Analysis for $C_{28}H_{39}NO_7$: Calcd: C, 67.04; H, 7.84; N, 2.79; Found: C, 66.82; H, 7.73; N, 2.58.

EXAMPLE 30

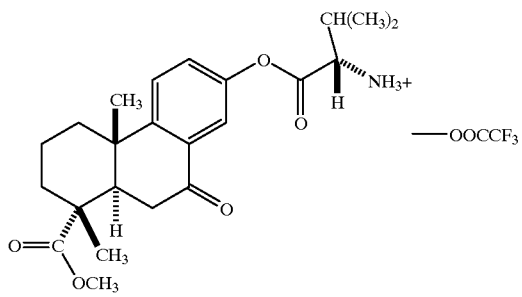

The compound was prepared substantially in accordance with the procedure detailed in Example 26, using the compound of Example 29.

Yield: 99% yield. IR(KBr): 3068, 2943, 1758, 1722 and 1668 cm$^{-1}$. $^1$H NMR (300 MHz, CDCl$_3$): δ 7.68 (m, 1H); 7.40 (m, 2H); 4.08 (d, J=4.8 Hz, 1H); 3.65 (s, 3H); 2.70 (m, 2H); 2.30–2.40 (m, 2H); 1.70–1.90 (m, 6H); 1.34 (s, 3H); 1.26 (s, 3H); 1.16 (d, J=2.9 Hz, 3H) and 1.14 (d, J=2.9 Hz, 3H). MS(FD): m/e free base 402 (M+). Elemental Analysis for $C_{25}H_{32}NO_7$: Calcd: C, 58.25; H, 6.26; N, 2.72; Found: C, 57.98; H, 6.32; N, 2.64.

EXAMPLE 31

A.

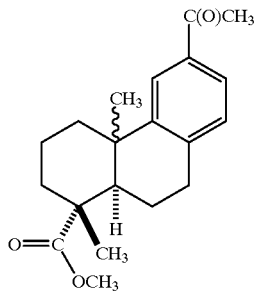

A mixture of 4.0 g (14.7 mmol) of the compound of Example 14A and 1.2 ml (16.9 mmol) of acetyl chloride in 60 ml of carbon disulfide to a suspension of 2.6 mg (19.5 mmol) of anhydrous aluminum chloride in 100 ml of carbon disulfide, via dropping funnel. The reaction mixture was refluxed for 1 hour and then the carbon disulfide was removed by downward distillation. The resultant residue was cautiously quenched by the addition of 100 ml of 0.2N HCl. The desired compound was extracted using 100 ml of $CH_2Cl_2$, dried over $Na_2SO_4$, filtered and then concentrated in vacuo to provide a dark red oil. This oil was purified using flash chromatography (SiO$_2$, eluent of 20% Et$_2$O in hexanes).

Yield: 1.7 g of an oil (87% based on recovered starting material). $^1$H NMR (300 MHz, CDCl$_3$): δ 7.90 (d, J=4 Hz, 1H); 7.75 (d, J=4 Hz, 0.5H); 7.63 (d, J=4 Hz, 0.5H); 7.37 (d, J=6 Hz, 0.5H); 7.10 (d, J=6 Hz, 0.5H); 3.70 (s, 1.5H); 3.68 (s, 1.5H); 2.92 (m, 2H); 2.60 (s, 3H); 2.00–2.50 (m, 3H); 1.40–1.98 (m, 6H); 1.29 (s, 1.5H); 1.26 (s, 1.5H); 1.24 (s, 1.5H) and 1.10 (s, 1.5H).

B.

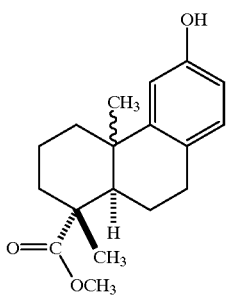

A mixture of 1.7 g (5.4 mmol) of the compound of Example 31A, 1.9 g (5.5 mmol) of 50% 3-chloroperoxybenzoic acid, 18 mg (0.095 mmol) of p-toluene sulfonic acid monohydrate in 25 ml of 1,2-dimethyoxyethane was refluxed for 3 hours, under $N_2$. After cooling, the reaction mixture was diluted with $Et_2O$ and washed sequentially with 10% potassium iodide, 10% sodium thiosulfate, a saturated $NaHCO_3$ solution and brine, dried over $Na_2SO_4$, filtered and then concentrated to provide a resin which was dissolved in 25 ml of MeOH and 10 ml of $H_2O$ containing 1.6 g (19.0 mmol) of $NaHCO_3$. The mixture was refluxed for 1.5 hours, cooled, filtered and concentrated in vacuo to provide a residue which was partitioned between $H_2O$ and $Et_2O$. The resulting layers were separated and the organic layer was washed sequentially with 1N HCl and brine, dried over $Na_2SO_4$, filtered and concentrated in vacuo Yield: 1.55 g (99%). $^1$H NMR (300 MHz, $CDCl_3$): δ 6.85 (m, 1H); 6.70 (d, J=6 Hz, 1H); 6.55 (dd, J=6 Hz, 1H); 3.63 (s, 3H); 2.80 (m, 2H); 1.90–2.30 (m, 3H); 1.40–1.88 (m, 6H); 1.25 (s, 1.5H); 1.20 (s, 1.5H); 1.17 (s, 1.5H) and 1.02 (s, 1.5H).

C.

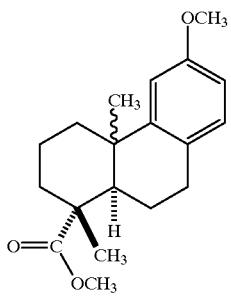

To a suspension of 1.55 g (5.4 mmol) of the compound of Example 31B and 275 mg (6.87 mmol) of 60% NaH on mineral oil in 50 ml of anhydrous DMF, was added 0.5 ml (7.50 mmol) of idodomethane, under $N_2$. The reaction mixture was stirred for 1 hour and then cautiously quenched by the dropwise addition of brine. The reaction mixture was partitioned between $Et_2O$ and brine. The resultant layers were separated and the organic layer was dried over $Na_2SO_4$, filtered and concentrated in vacuo to provide a residue which was purified using flash chromatography ($SiO_2$, eluent of 20% $Et_2O$ in hexanes).

Yield: 1.3 g of a clear light yellow oil (88.5% based on recovered starting material). $^1$H NMR (300 MHz, $CDCl_3$): δ 7.00 (d, J=6 Hz, 1H); 6.82 (m, 1H); 6.70 (m, 1H); 3.80 (s, 3H); 3.70 (s, 3H); 2.80 (m, 2H); 2.00–2.40 (m, 3H); 1.40–1.90 (m, 6H); 1.25 (s, 1.5H); 1.20 (s, 3H); 1.10 (s, 1.5H).

Note: The reaction mixture also contained 200 mg of the compound of Example 31A.

D.

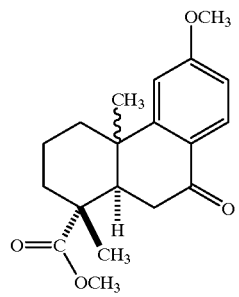

The compound was prepared substantially in accordance with the procedure detailed in Example 14B, using 1.3 g (4.3 mmol) of the compound of Example 31C. The crude material was purified using flash chromatography ($SiO_2$, eluent of 20% $Et_2O$ in hexanes).

Yield: 820 mg of an oil (60.5%). $^1$H NMR (300 MHz, $CDCl_3$): δ 8.00 (m, 1H); 6.80 (m, 2H); 3.87 (s, 1.5H); 3.85 (s, 1.5H); 3.63 (s, 1.5H); 3.61 (s, 1.5H); 3.01 (dd, J=5, 12 Hz, 0.5H); 2.70 (m, 1.5H); 2.40 (m, 2H); 1.40–1.95 (m, 5H); 1.32 (s, 1.5H); 1.30 (s, 1.5H); 1.22 (s, 1.5H); 0.65 (s, 1.5H).

E.

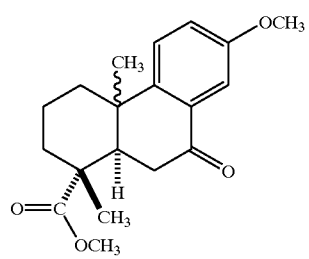

The compound was isolated from Example 31D.

Yield: 35.4 mg of an oil.

F.

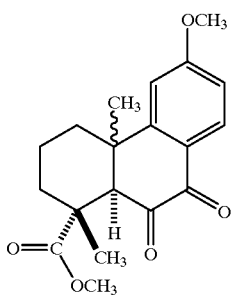

The compound was isolated from Example 31D.

Yield: 150 mg of an oil (10.6%). $^1$H NMR (300 MHz, $CDCl_3$): δ 8.17 (d, J=6 Hz, 1H); 6.95 (m, 1H); 6.80 (m, 1H); 3.90 (s, 3H); 3.70 (s, 3H); 3.36 (s, 0.5H); 2.50 (m, 1.5H); 1.80–2.10 (m, 1H); 1.42–1.80 (m, 4H); 1.40 (s, 1.5H); 1.20 (s, 1.5H); 1.17 (s, 1.5H); 0.65 (s, 1.5H).

Example 31G-deleted

H.

The compound was prepared substantially in accordance with the procedure detailed in Example 15A, using 975 mg (3.08 mmol) of the compound of Example 31D. The crude material was purified using flash chromatography (SiO$_2$, eluent of 15% of Et$_2$O in hexanes).

Yield: 532.6 mg (44%). $^1$H NMR (300 MHz, CDCl$_3$): δ 8.03 (d, J=6 Hz, 1H); 6.81 (m, 2H); 4.50 (s, 1H); 3.90 (s, 3H); 3.75 (s, 3H); 3.21 (s, 1H); 2.40 (m, 1H); 1.60–2.00 (m, 5H); 1.58 (s, 3H) and 0.60 (s, 3H).

I.

The compound was isolated from Example 31H. Yield: 465.1 mg of an oil (38%). $^1$H NMR (300 MHz, CDCl$_3$): δ 8.00 (d, J=6 Hz, 1H); 6.85 (m, 2H); 4.97 (d, J=9 Hz, 1H); 3.90 (s, 3H); 3.62 (s, 3H); 3.22 (d, J=9 Hz, 1H); 2.30 (m, 1H); 1.80 (m, 5H); 1.48 (s, 3H) and 1.28 (s, 3H).

Example 31J-deleted

K.

The compound was prepared substantially in accordance with the procedure detailed in Example 16, using 465 mg (1.17 mmol) of the compound of Example 31I.

Yield: 328 mg of a clear oil (89%). IR(CHCl$_3$): 2942, 1721, 1667 and 1596 cm$^{-1}$. $^1$H NMR (300 MHz, CDCl$_3$): δ 8.01 (d, J=9.2 Hz, 1H); 6.85 (s, 1H); 6.81 (d, J=2.6 Hz, 1H); 3.90 (s, 3H); 3.66 (s, 3H); 2.70 (m, 2H); 2.30 (m, 2H); 1.60–1.90 (m, 5H); 1.35 (s, 3H) and 1.26 (s, 3H). MS(FD): m/e 316 (M+).

EXAMPLE 32

The compound was prepared substantially in accordance with the procedure detailed in Example 6, using the compound of Example 31K.

Yield: 61%. m.p. 162–165° C. IR(CHCl$_3$): 3018, 2951, 1720 and 1600 cm$^{-1}$. $^1$H NMR (300 MHz, CDCl$_3$): δ 7.81 (d, J=6 Hz, 1H); 6.82 (m, 3H); 3.90 (s, 3H); 3.70 (s, 3H); 2.62 (d, J=6 Hz, 2H); 2.20–2.43 (m, 2H); 1.60–1.90 (m, 5H); 1.40 (s, 3H) and 1.10 (s, 3H). MS(FD): m/e 331 (M+). Elemental Analysis for C$_{19}$H$_{25}$NO$_4$: Calcd: C, 68.86; H, 7.60; N, 4.23; Found: C, 68.79; H, 7.42; N, 4.33.

As noted above, the compounds of the present invention are useful for inhibiting an envelope virus that undergoes hemagglutinin-mediated fusion with a host cell. Thus, the claimed compounds may be used to treat or prevent a viral infection where the virus is an envelope virus that undergoes hemagglutinin-mediated fusion which comprises administering to an virus-infected cell, a cell susceptible to infection or a mammal in need thereof an effective amount of a compound of formula I or a pharmaceutically acceptable salt thereof. The claimed compounds may also be used to inhibit viral replication in an envelope virus that undergoes hemagglutinin-mediated fusion which comprises administering to a virus-infected cell, a cell susceptible to infection or a mammal in need thereof, an effective amount of a compound of formula I or a pharmaceutically acceptable salt thereof.

The term "effective amount" as used herein, means an amount of a compound of the present invention which is capable of inhibiting the hemagglutinin mediated fusion of the virus with the host cell. The inhibition contemplated by the present method includes both therapeutic and prophylactic treatment, as appropriate. The specific dose of compound administered according to this invention to obtain therapeutic and/or prophylactic effects will, of course, be determined by the particular circumstances surrounding the case, including, for example, the compound administered, the route of administration, the condition being treated and the individual being treated. A typical daily dose (administered in single or divided doses) will contain a dosage level of from about 0.01 mg/kg to about 50 mg/kg of body weight of an active compound of this invention. Preferred daily doses generally will be from about 0.05 mg/kg to about 20 mg/kg and ideally from about 0.1 mg/kg to about 10 mg/kg.

The compounds can be administered by a variety of routes including oral, rectal, transdermal, subcutaneous, intravenous, intramuscular and intranasal. The compounds of the present invention are preferably formulated prior to administration. Therefore, another embodiment of the present invention is a pharmaceutical formulation comprising an effective amount of a compound of formula I or a pharmaceutically acceptable salt thereof and a pharmaceutically acceptable carrier, diluent or excipient therefor.

The active ingredient in such formulations comprises from 0.1% to 99.9% by weight of the formulation. By "pharmaceutically acceptable" it is meant that the carrier, diluent or excipient is compatible with the other ingredients of the formulation and not deleterious to the recipient thereof.

The present pharmaceutical formulations are prepared by known procedures using known and readily available ingredients. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols, (as a solid or in a liquid medium), ointments containing, for example, up to 10% by weight of the active compound, soft and hard gelatin capsules, suppositories, sterile injectable solutions, sterile packaged powders and the like.

The following experiments were carried out to demonstrate the ability of the compounds of the present invention to inhibit influenza.

In Vitro CPE/XTT Assay

MDCK cells were dispersed in a microtiter plate (96 wells) at 10,000 cells per well with Medium 199 containing Earl's balanced salt solution (EBSS), 1% fetal bovine serum (FBS), penicillin (100 units/ml) and streptomycin (100 μg/ml). After standing overnight at 37° C. in a carbon dioxide ($CO_2$) incubator, the MDCK cells were infected with ~0.1 moi (mutiplicity of infection) of influenza virus (i.e. A/Kawasaki/89 or B/Hong Kong and B/Great Lakes) at 0.03 moi. After allowing the virus to adsorb to the cells for 1–2 hours, medium containing serial dilutions of drug or medium alone was added to the wells. The resultant mixtures were incubated for 2–3 days (until extensive cpe was apparent in medium alone wells). The antiviral effect of a test compound was assessed by performing the following XTT assay.

A fresh solution (0.4 mg/ml) of XTT [2,3-bis(methoxy-4-nitro-5-sulfophenyl)-2H-tetraazolium-5-carboxanilide, inner salt, sodium salt] in warm medium without FBS was prepared. For each 5 ml of the XTT solution, 25 μl of 5 mM PMS (phenazine methosulfate) in phosphate buffer saline was added. After withdrawing the cultured supernatant, 100 μl of the freshly prepared XTT/PMS mixture was added to each of the microtiter wells. The wells were then incubated at 37° C. (under $CO_2$) for 3–4 hours or until color change is prominent. The absorbance at 450 nm (ref. 650 nm) was read in a spectrophotometer. The concentration of test compound required to cause 50% cytotoxic effect ($TC_{50}$) relative to a control with no drug and no virus present and which inhibits the development of virus cytopathic effect (cpe) by 50% ($IC_{50}$) or 90% ($IC_{90}$) was determined from the linear portion of each dose response curve.

Using this CPE/XTT assay, the $IC_{50}$ of the compounds of formula I was determined to be in the range of 1.0–2.4 μg/ml for influenza A/Kawasaki/89 and in the range of 8–47 μg/ml for influenza B/Lee.

Plaque Reduction Assay

Susceptible MDCK cells were grown in 6 well tissue culture treated cluster plates at $1 \times 10^6$ cells/well in Minimum 199 with 1 percent fetal bovine serum, penicillin (100 units/ml) and streptomycin (100 μg/ml). After overnight incubation at 37° C., the growth medium was removed and 0.2 ml/well of an appropriate dilution of virus was added. After adsorption for 1–2 hour at room temperature, the infected cell sheet was overlaid with equal parts of 1.5% sterile agarose solution and a twofold concentration of medium 199 (with 2% fetal bovine serum, 100 units/ml of penicillin and 100 μg/ml streptomycin) containing varying concentrations of compounds.

The compounds were dissolved in DMSO at a concentration of 20 mg/ml and an aliquot was diluted to the desired concentration in DMSO and then added to the agar medium mixture. The plates were incubated in a $CO_2$ incubator at 37° C. until the DMSO control wells contained plaques of optimal size. Then, a solution containing 10 percent formalin and 2 percent sodium acetate was added to each well to inactivate the virus and fix the cell sheet to the plastic surface. The fixed cell sheets were stained with 0.5 percent crystal violet and the plaques were counted. Results from duplicate wells at each concentration were averaged and compared with DMSO control wells. The inhibition of plaque formation by 50 or 90 percent ($IC_{50}$ or $IC_{90}$) was calculated from the linear region of the inhibition concentration curve using the method of Reed and Muench; Am. J. Hyg., vol. 27, pages 493–497 (1958).

Using this plaque reduction assay, the $IC_{50}$ of the compounds of formula I was determined to be in the range of 0.02–100 μg/ml for influenza A/Kawasaki and was determined to be in the range of 1.5–60.5 μg/ml for influenza B/Lee.

We claim:
1. A compound of the formula

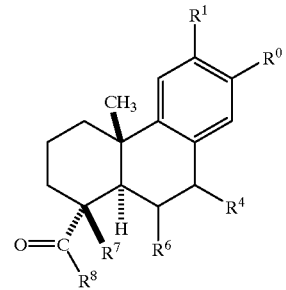

wherein:

$R^0$ and $R^1$ are independently hydrogen, hydroxy, $C_1-C_6$ alkyl, $C_1-C_6$ alkoxy, hydroxy($C_1-C_6$ alkyl), sulfhydryl, sulfamyl, —$SO_2$—Cl, —S—C(O)—N($CH_3$)$_2$, amino, $C_1-C_4$ alkylamino, di($C_1-C_4$ alkyl)amino, $C_1-C_4$ alkylsulfonylamino, di($C_1-C_4$ alkylsulfonyl)amino, —$X^0$—O—C(O)—$C_1-C_4$ alkyl, —O—($X^1$)$_i$, —C(O)—$X^3$, —N—C(O)—$R^2$ or —O—$R^3$;

$X^0$ is a bond or divalent ($C_1-C_6$ alkyl);

$X^1$ is an amino acid ester of glycine, alanine or valine;

i is 1, 2 or 3;

$X^3$ is $C_1-C_6$ alkyl, $C_1-C_6$ alkoxy, halo($C_1-C_6$ alkyl), hydroxy($C_1-C_6$ alkyl) or phenyl;

$R^2$ is $C_1-C_4$ alkyl, $C_1-C_4$ alkoxy, halo($C_1-C_4$ alkyl), hydroxy($C_1-C_4$ alkyl), phenyl, p-methoxy-phenyl, p-fluoro-phenyl, naphthyl, or cyclohexyl;

$R^3$ is $C_2$-$C_6$ alkenyl, —$CH_2$—$R^{3a}$, —$C(O)$—$R^{3b}$, —$C(S)$—$R^{3c}$, —$C(CH_3)_2C(O)NH_2$, phenyl or a group of the formula

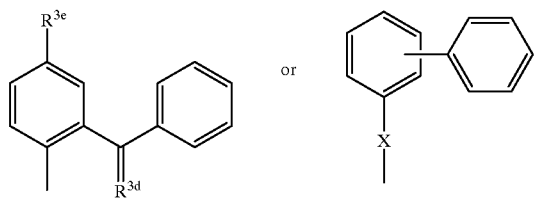

$R^{3a}$ is phenyl, p-fluorophenyl, cyclohexyl, cyclopentyl, cyclopropyl or naphthyl;

$R^{3b}$ is benzyloxy, $C_1$-$C_6$ alkoxy, halo($C_1$-$C_4$ alkoxy), amino, $C_1$-$C_4$ alkylamino or di($C_1$-$C_4$ alkyl)amino;

$R^{3c}$ is amino, $C_1$-$C_4$ alkylamino or di($C_1$-$C_4$ alkyl)amino;

$R^{3d}$ is oxygen, hydroximino, hydrazino or =CHZ;

Z is hydrogen, $C_1$-$C_4$ alkyl, halogen, di($C_1$-$C_4$ alkyl)amino, $C_1$-$C_4$ alkoxycarbonyl, carbamoyl($C_1$-$C_4$ alkyl), N-($C_1$-$C_4$ alkyl)carbamoyl or N,N-di($C_1$-$C_4$ alkyl)carbamoyl;

$R^{3e}$ is hydrogen, nitro or trifluoromethyl;

X is a bond or —($CH_2$)—;

$R^4$ is =N—$R^5$;

$R^5$ is hydroxy, amino, $C_1$-$C_4$ alkylamino, di($C_1$-$C_4$ alkyl)amino, $C_1$-$C_4$ alkoxy, benzyloxy, or —O—$CH_2$—C(O)—$R^{5a}$;

$R^{5a}$ is hydroxy or $C_1$-$C_4$ alkoxy;

$R^6$ is hydrogen, halo, $C_1$-$C_4$ alkyl or =O;

$R^7$ is hydrogen or $C_1$-$C_4$ alkyl;

$R^8$ is hydroxy, halo, or $C_1$-$C_6$ alkoxy;

or a pharmaceutically acceptable salt thereof.

2. The compound of claim 1 wherein $R^0$ is hydrogen, hydroxy, $C_1$-$C_6$ alkyl, $C_1$-$C_6$ alkoxy, hydroxy($C_1$-$C_6$ alkyl), —$X^0$—O—C(O)—$C_1$-$C_4$ alkyl, —O—($X^1$)$_i$, —C(O)—$X^3$ or —O—$R^3$;

$R^1$ is hydrogen, hydroxy, $C_1$-$C_6$ alkoxy, sulfhydryl, sulfamyl, —$SO_2$—Cl, amino, di($C_1$-$C_4$ alkylsulfonyl)amino —C(O)—$X^3$, —N—C(O)—$R^2$ or —O—$R^3$;

$X^0$ is a bond or divalent($C_1$-$C_6$ alkyl);

$X^1$ is an amino acid ester of glycine, alanine or valine;

i is 1 or 2;

$X^3$ is $C_1$-$C_6$ alkyl;

$R^2$ is hydroxy($C_1$-$C_4$ alkyl);

$R^3$ is $C_2$-$C_6$ alkenyl, —$CH_2$—$R^{3a}$, —$C(O)$—$R^{3b}$, —$C(S)$—$R^{3c}$, —$C(CH_3)_2C(O)NH_2$ or a group of the formula:

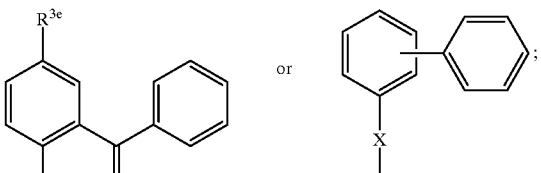

$R^{3a}$ is phenyl, or p-fluorophenyl;

$R^{3b}$ is halo($C_1$-$C_4$ alkoxy) or di($C_1$-$C_4$ alkyl)amino;

$R^{3c}$ is di($C_1$-$C_4$ alkyl)amino;

$R^{3d}$ is oxygen or hydroximino;

$R^{3e}$ is hydrogen, nitro or trifluoromethyl;

X is a bond;

$R^4$ is =N—$R^5$;

$R^5$ is hydroxy, amino, di($C_1$-$C_4$ alkyl)amino, $C_1$-$C_4$ alkoxy, or —O—$CH_2$—C(O)—$R^{5a}$;

$R^6$ is hydrogen, chloro, bromo, methyl or =O;

$R^7$ is hydrogen or methyl;

$R^8$ is hydroxy, chloro, or methoxy;

or a pharmaceutically acceptable salt thereof.

3. The compound of claim 2 wherein $R^0$ is hydrogen, hydroxy, $C_1$-$C_6$ alkoxy, —O—($X^1$)$_i$, —$X^0$—O—C(O)—$C_1$-$C_4$ alkyl or —O—$R^3$;

$R^1$ is hydrogen, hydroxy, $C_1$-$C_6$ alkoxy or —O—$R^3$;

$X^0$ is a bond;

$X^1$ is an amino acid ester of glycine, alanine or valine;

i is 1 or 2;

$R^3$ is $C_2$-$C_6$ alkenyl, or —$CH_2$—$R^{3a}$;

$R^{3a}$ is p-fluorophenyl;

$R^4$ is =N—$R^5$;

$R^5$ is hydroxy, or dimethylamino;

$R^6$ is hydrogen, bromo or =O;

$R^7$ is methyl; and $R^8$ is methoxy;

or a pharmaceutically acceptable salt thereof.

4. The compound of claim 3 wherein $R^0$ is hydrogen, hydroxy, $C_1$-$C_4$ alkoxy, —O—($X^1$)$_i$, —O—C(O)methyl or —O—$R^3$;

$R^1$ is hydrogen, hydroxy, $C_1$-$C_4$ alkoxy or —O—$R^3$;

$X^1$ is an amino acid ester of glycine, alanine or valine;

$R^4$ is =N—$R^5$;

$R^5$ is hydroxy;

$R^6$ is hydrogen;

or a pharmaceutically acceptable salt thereof.

5. The compound of claim 1 wherein $R^4$ is =N—OH.

6. The compound of claim 2 wherein $R^4$ is =N—OH.

7. The compound of claim 3 wherein $R^4$ is =N—OH.

* * * * *